(12) United States Patent
Christadoss et al.

(10) Patent No.: US 8,501,705 B2
(45) Date of Patent: Aug. 6, 2013

(54) METHODS AND MATERIALS FOR TREATING AUTOIMMUNE AND/OR COMPLEMENT MEDIATED DISEASES AND CONDITIONS

(75) Inventors: Premkumar Christadoss, League City, TX (US); Erdem Tuzun, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/928,945

(22) Filed: Dec. 23, 2010

(65) Prior Publication Data
US 2011/0104156 A1 May 5, 2011

Related U.S. Application Data

(63) Continuation-in-part of application No. 10/571,379, filed as application No. PCT/US2004/029673 on Sep. 11, 2004, now Pat. No. 7,923,010.

(60) Provisional application No. 60/502,086, filed on Sep. 11, 2003.

(51) Int. Cl.
| | |
|---|---|
| *A01N 43/04* | (2006.01) |
| *C07H 21/02* | (2006.01) |
| *C07H 21/04* | (2006.01) |
| *C12Q 1/68* | (2006.01) |
| *C12P 19/34* | (2006.01) |

(52) U.S. Cl.
USPC ............. 514/44; 435/6; 435/91.1; 435/91.31; 435/455; 536/23.1; 536/24.31; 536/24.5

(58) Field of Classification Search
USPC .................. 435/6, 91.1, 91.31, 455; 514/1, 2, 514/44; 536/23.1, 24.5, 24.31
See application file for complete search history.

(56) References Cited

U.S. PATENT DOCUMENTS

| 7,691,997 B2 * | 4/2010 | Khvorova et al. | ........... 536/24.5 |
| 2001/0026928 A1 * | 10/2001 | Fung et al. | ................... 435/7.92 |
| 2002/0115614 A1 * | 8/2002 | Frank et al. | ..................... 514/14 |
| 2005/0019326 A1 | 1/2005 | Stahl | |

FOREIGN PATENT DOCUMENTS

WO    WO 02/44321    *    6/2002

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature rev., vol. 1, pp. 503-514 (2002).*
Holen et al., Nucleic Acids. Res., vol. 30, No. 8, pp. 1757-1766 (2002).*
Paroo et al., Trends in Biotech., vol. 22, No. 8, pp. 390-394 (2004).*
Christadoss, Premkumar, et al., "Classical Complement Pathway in Experimental Autoimmune Myasthenia Gravis Pathogenesis", Ann. N.Y. Academy of Sciences, 2008, 210-219, vol. 1132, New York Academy of Sciences.
Gunnarsson, I., et al., "Occurrence of anit-C1q anitbodies in IgA nephropathy", Nephrology Dialysis Transplantation, Nov. 1997, pp. 2263-2268, vol. 12 No. 11, European Renal Association-European Dialysis and Transplant Association.

* cited by examiner

*Primary Examiner* — Jane Zara

(57) ABSTRACT

Disclosed are methods for treating an autoimmune and/or complement mediated disease or condition in a subject. The methods include administering to the subject a compound which inhibits the subject's classical complement pathway. The methods include administering to the subject a compound which inhibits the subject's classical complement pathway. Compositions which include inhibitors of C1q, C1r, C1s, C2 or C4 and a pharmaceutically acceptable excipient are also described.

3 Claims, 27 Drawing Sheets

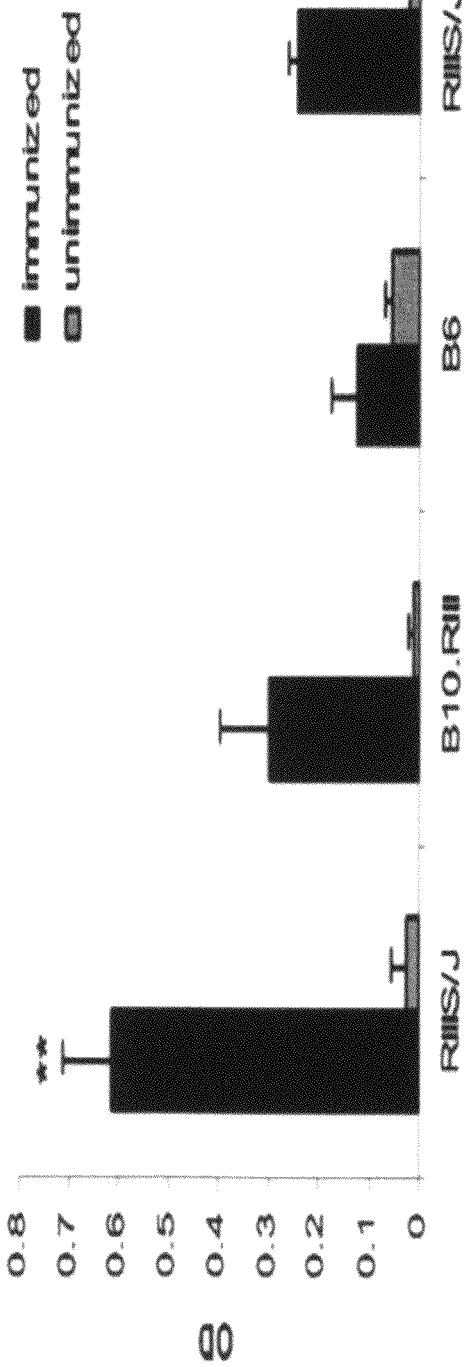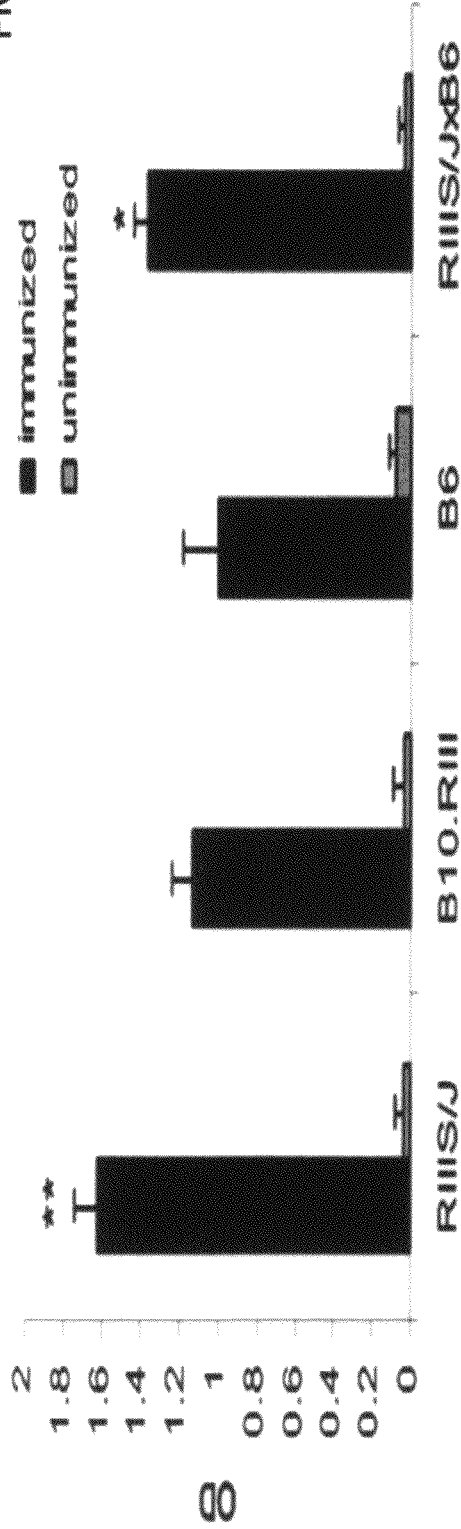

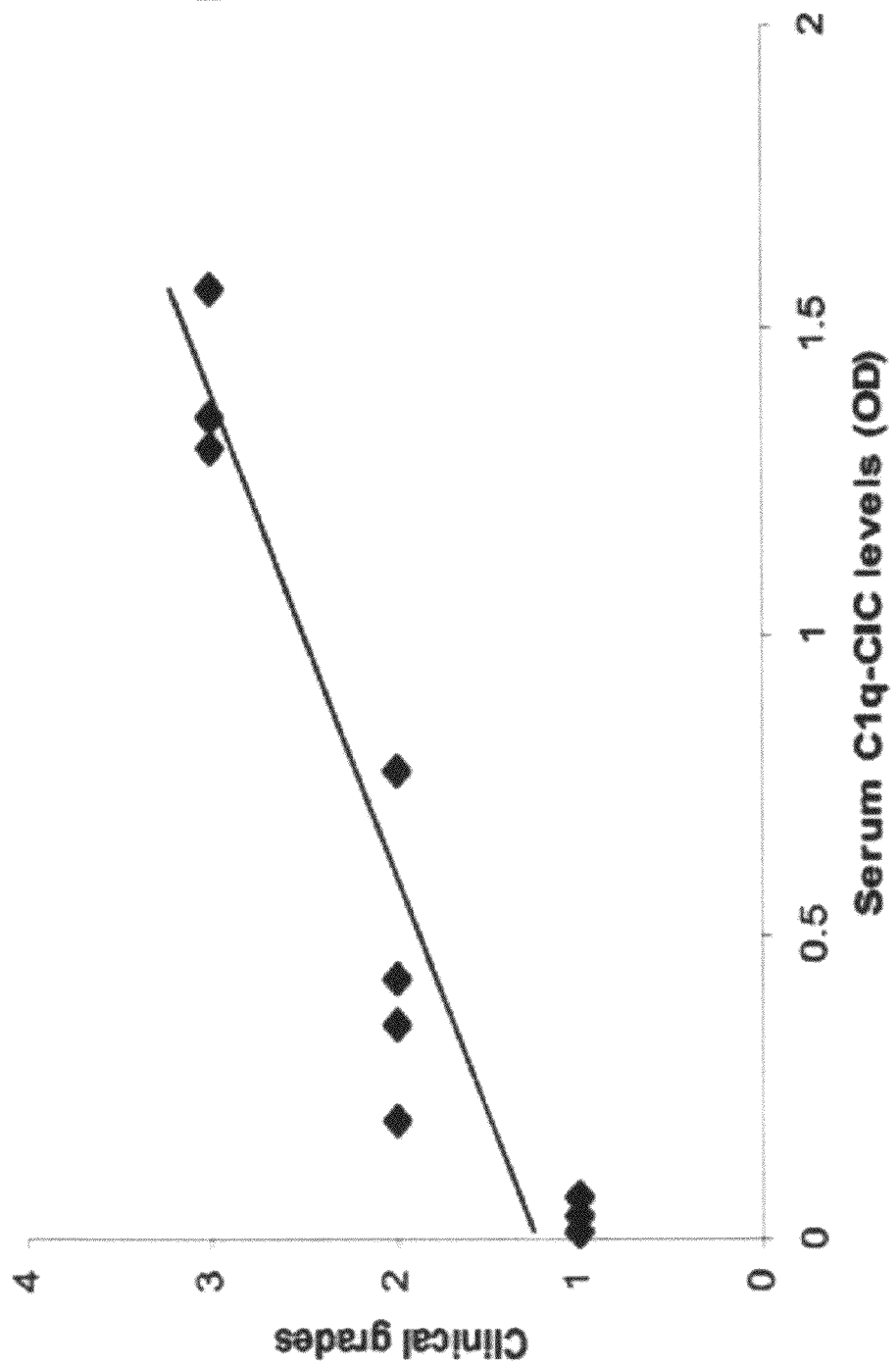

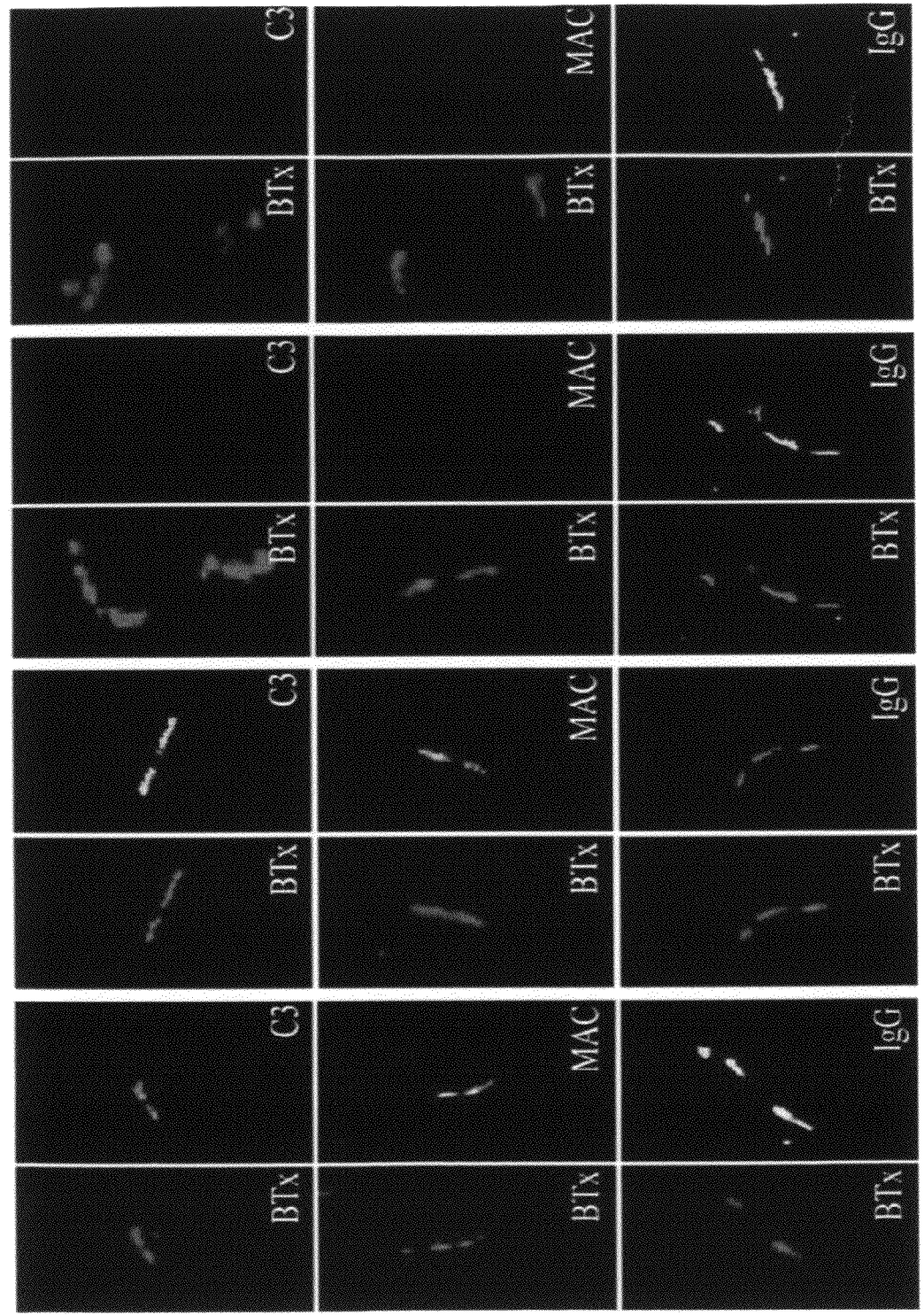

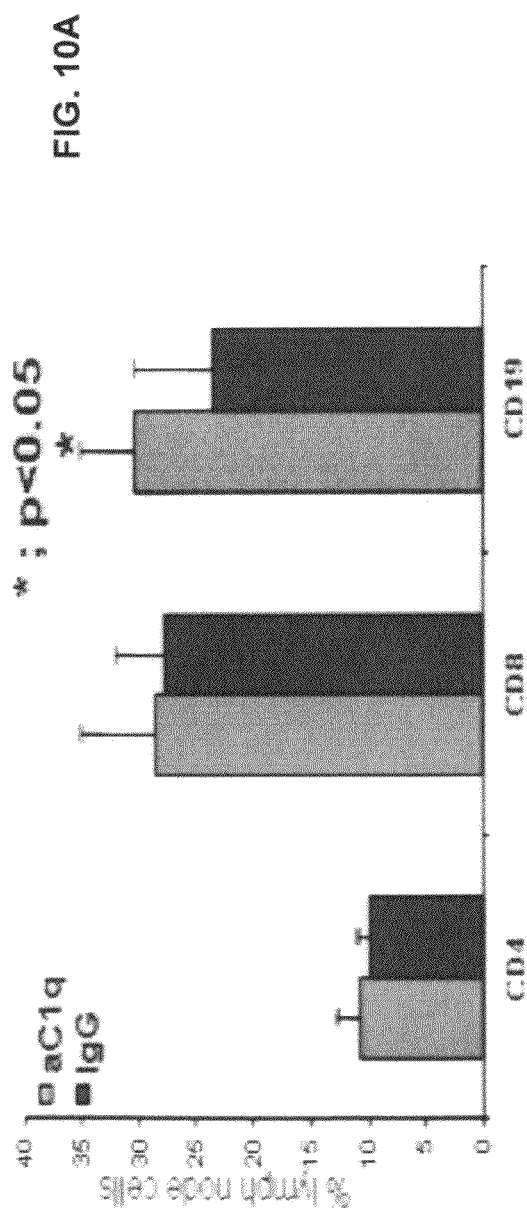
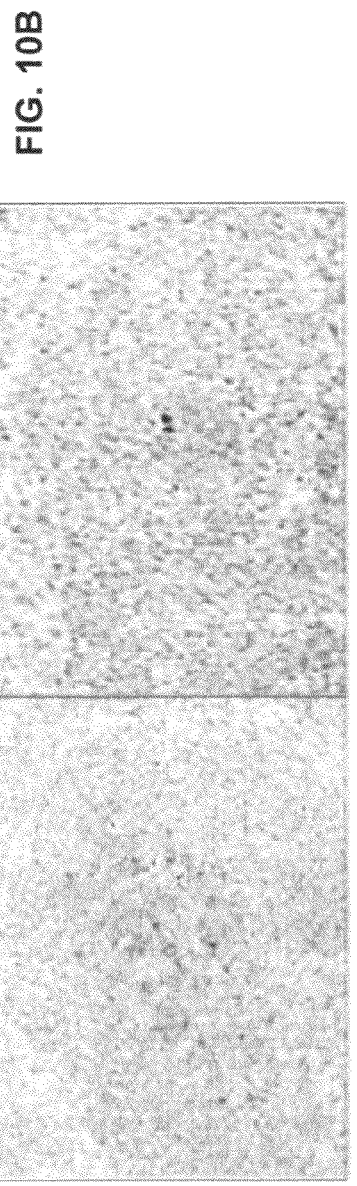

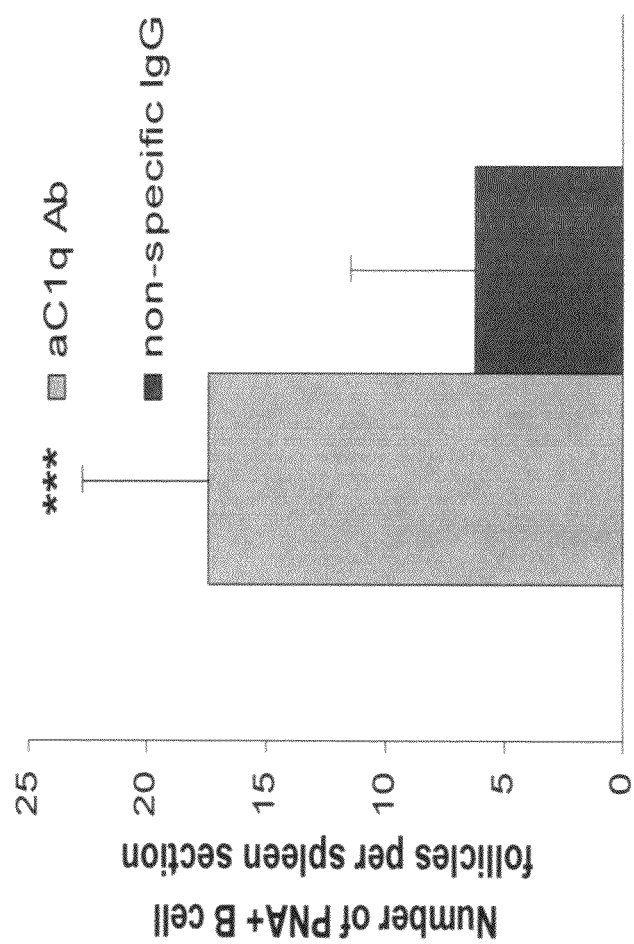

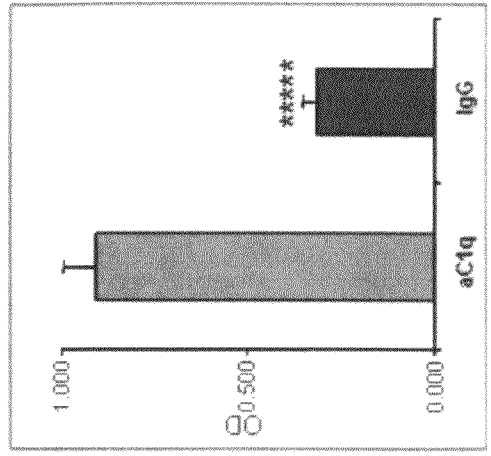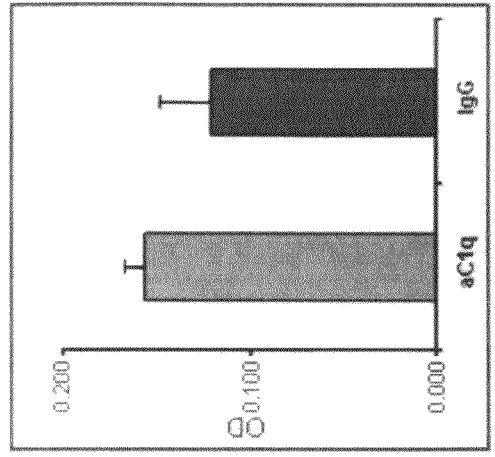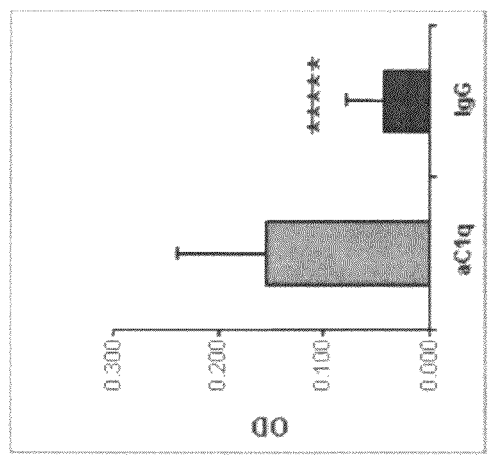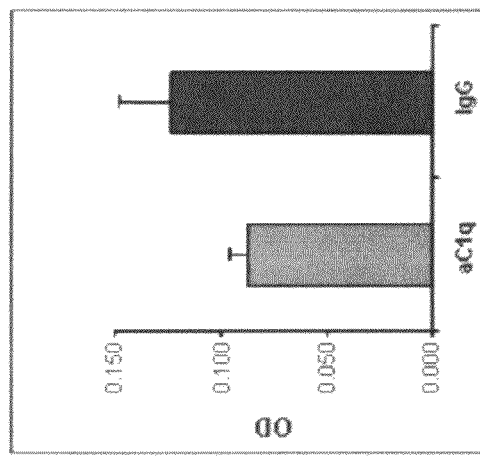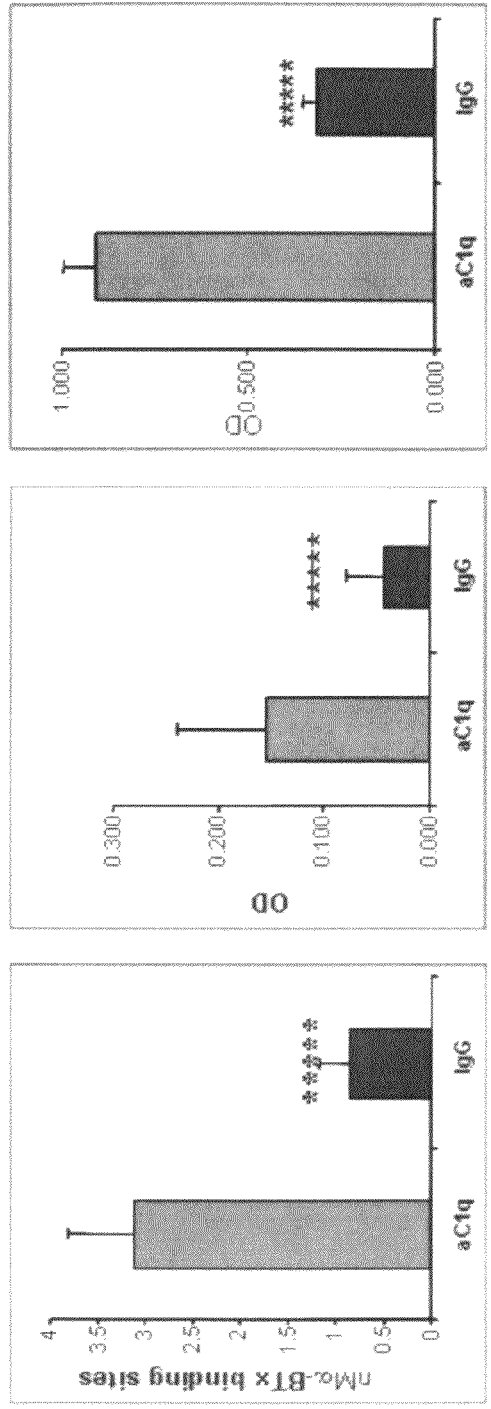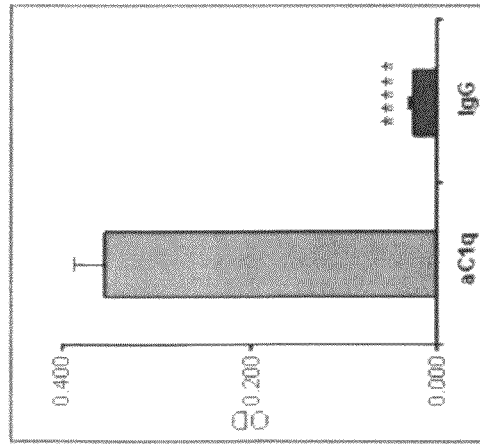

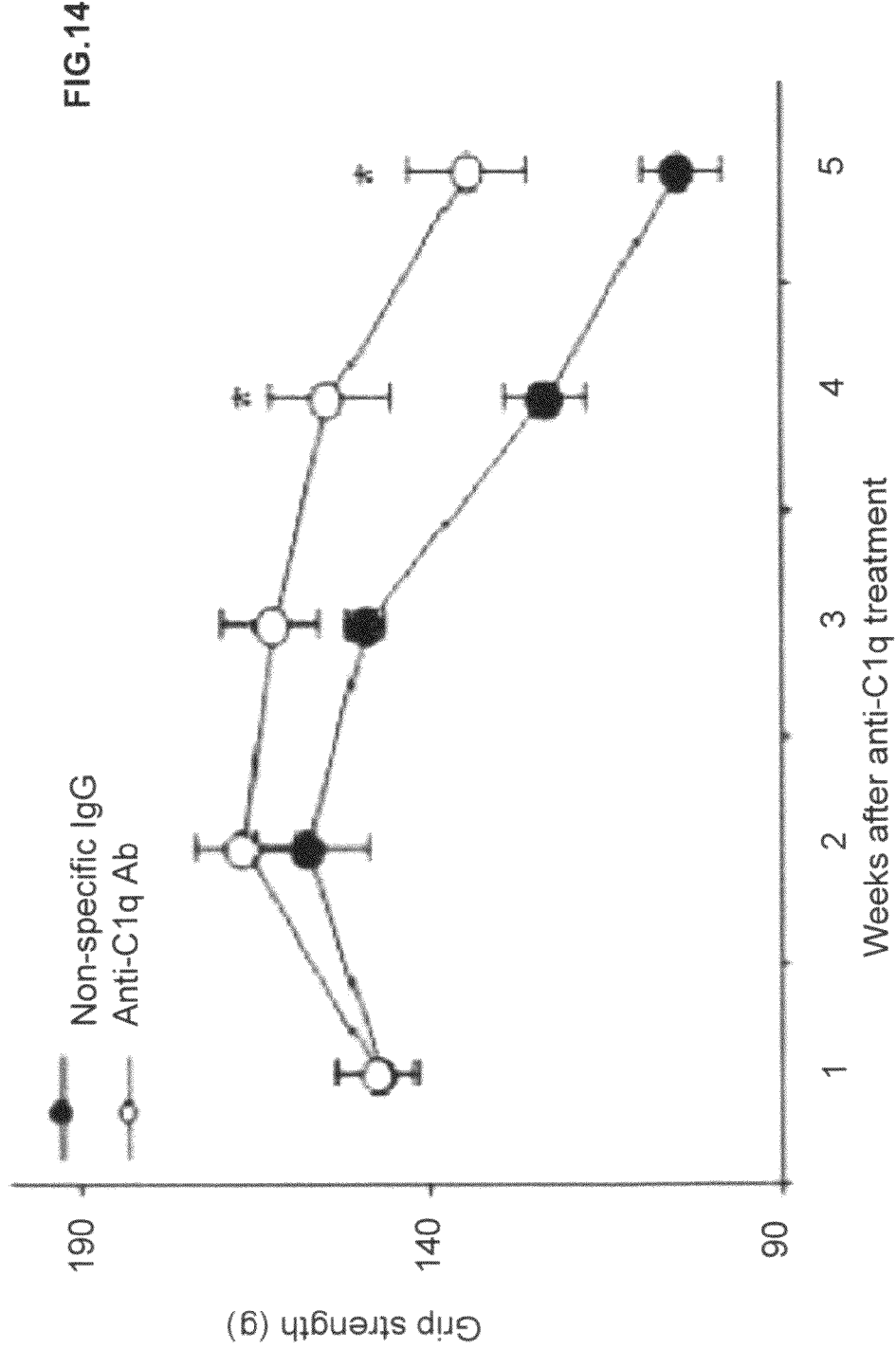

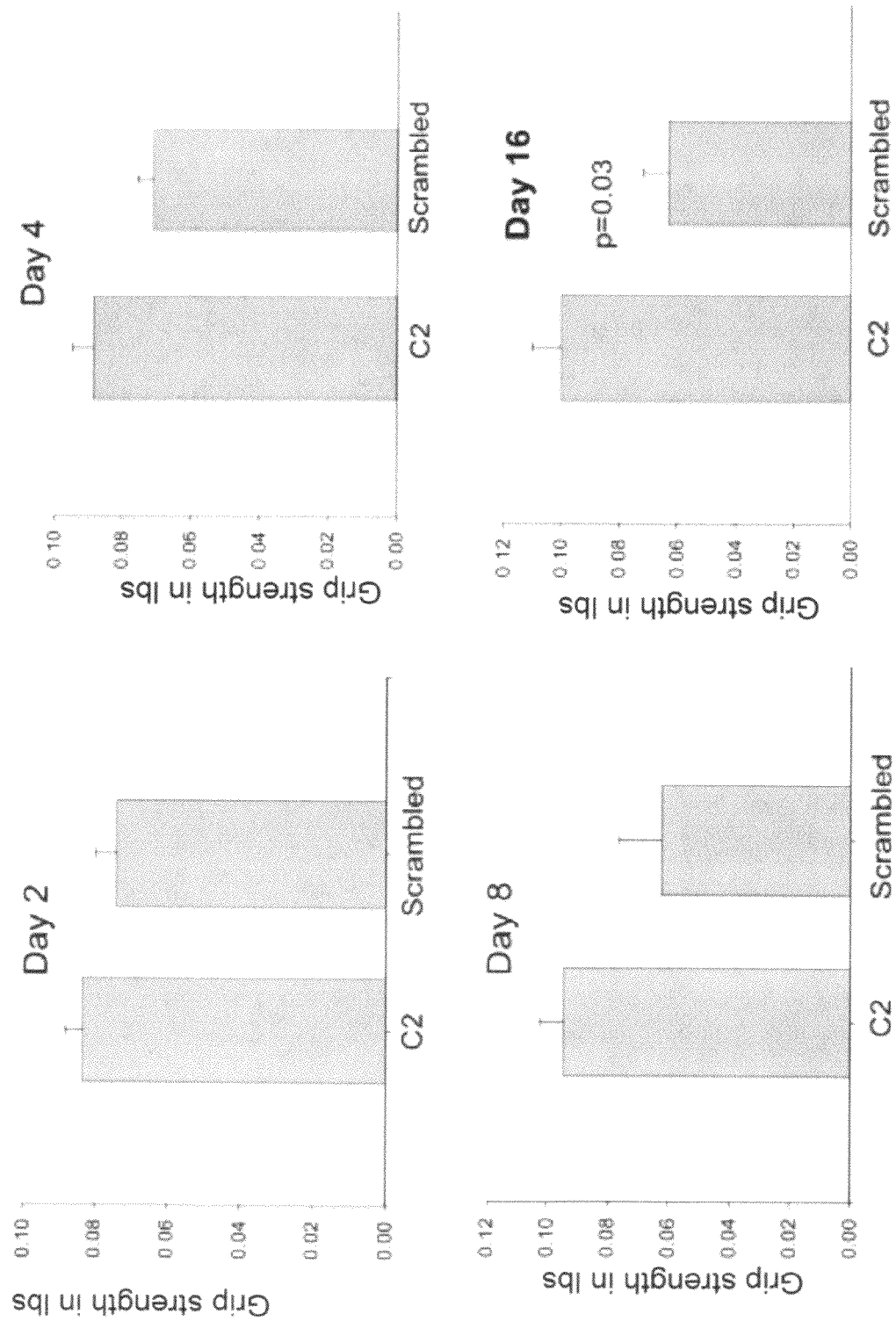

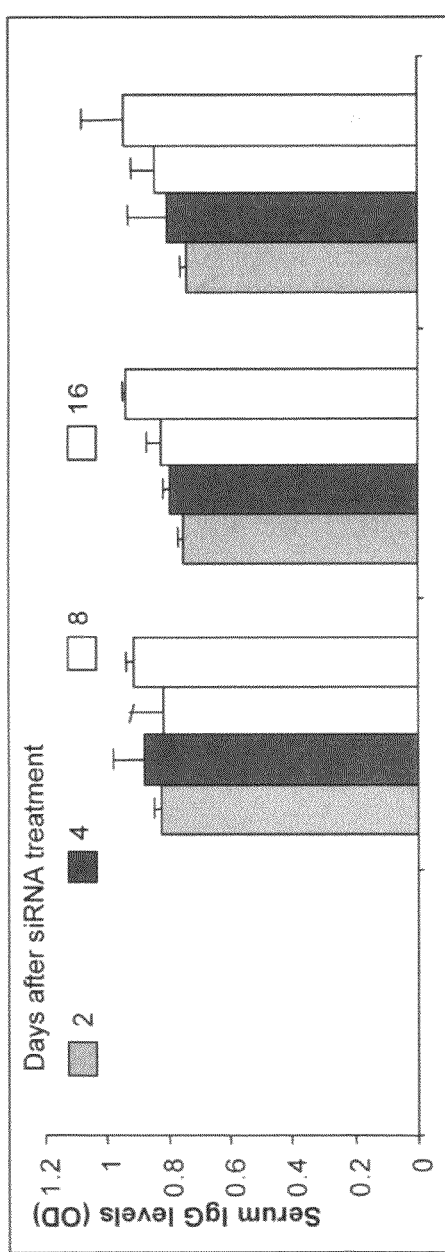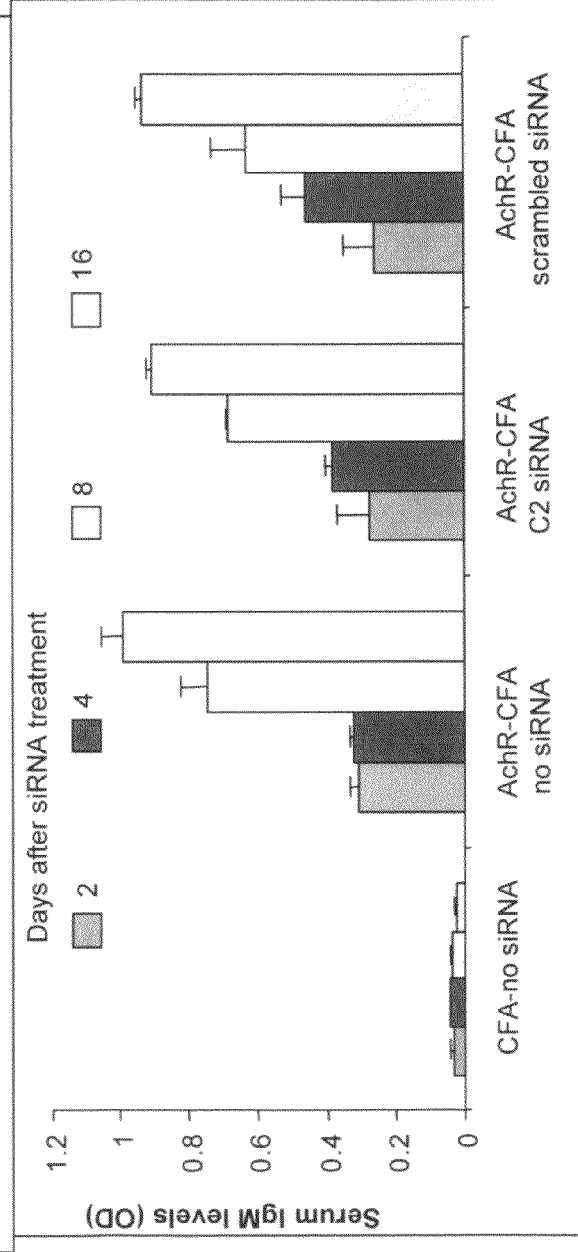

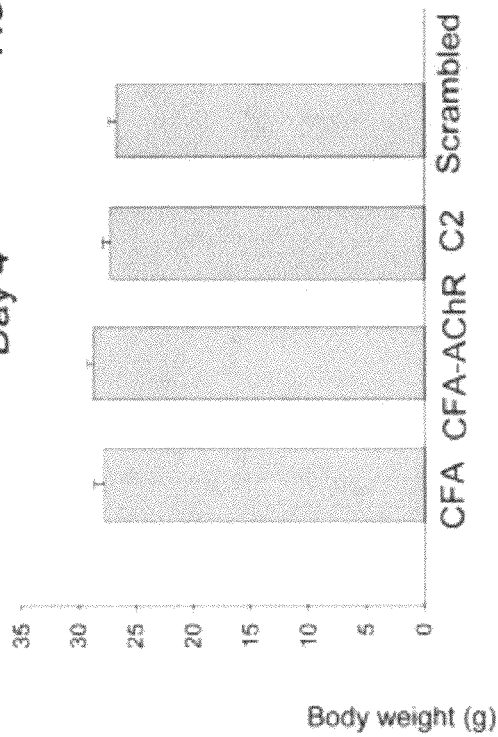
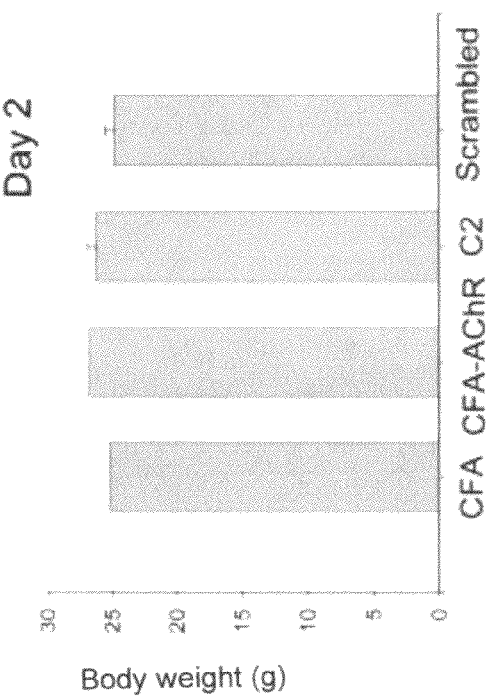
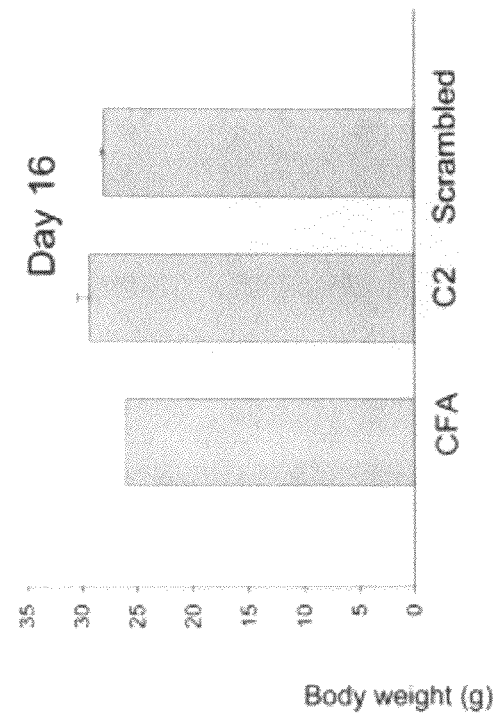
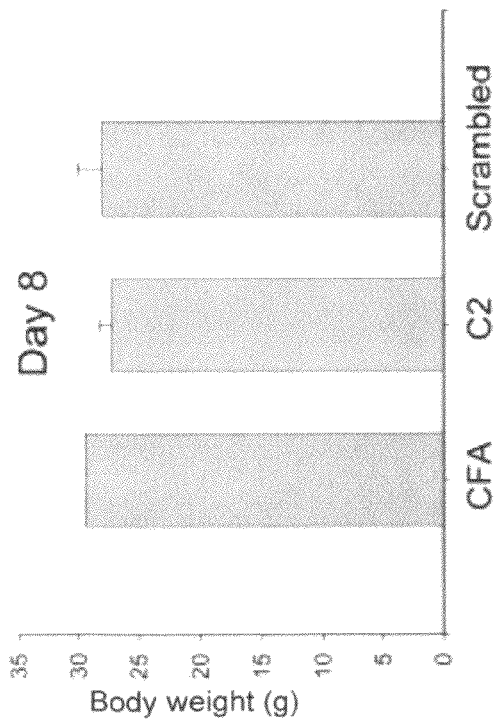
FIG. 21

FIG. 24

```
                        SEQUENCE LISTING

<160> NUMBER OF SEQ ID NOS: 37

<210> SEQ ID NO 1
<211> LENGTH: 5
<212> TYPE: PRT
<213> ORGANISM: Artificial sequence
<220> FEATURE:
<223> OTHER INFORMATION: C1q inhibiting peptide

<400> SEQUENCE: 1

Trp Tyr Val Asp Gly
1               5

<210> SEQ ID NO 2
<211> LENGTH: 4
<212> TYPE: PRT
<213> ORGANISM: Artificial sequence
<220> FEATURE:
<223> OTHER INFORMATION: C1q inhibiting peptide

<400> SEQUENCE: 2

Thr Lys Pro Arg
1

<210> SEQ ID NO 3
<211> LENGTH: 5
<212> TYPE: PRT
<213> ORGANISM: Artificial sequence
<220> FEATURE:
<223> OTHER INFORMATION: C1q inhibiting peptide

<400> SEQUENCE: 3

Gly Lys Glu Tyr Lys
1               5

<210> SEQ ID NO 4
<211> LENGTH: 24
<212> TYPE: PRT
<213> ORGANISM: Artificial sequence
<220> FEATURE:
<223> OTHER INFORMATION: C1q inhibiting peptide

<400> SEQUENCE: 4

Leu His Thr Asp Gly Asp Lys Ala Phe Val Asp Phe Leu Ser Asp Glu
1               5                   10                  15

Ile Lys Glu Glu Arg Lys Ile Gln
            20

<210> SEQ ID NO 5
<211> LENGTH: 14
<212> TYPE: PRT
<213> ORGANISM: Artificial sequence
<220> FEATURE:
<223> OTHER INFORMATION: C1q inhibiting peptide

<400> SEQUENCE: 5

Leu Glu Gln Gly Glu Asn Val Phe Leu Gln Ala Thr Leu Leu
1               5                   10
```

-continued

<210> SEQ ID NO 6
<211> LENGTH: 15
<212> TYPE: PRT
<213> ORGANISM: Artificial sequence
<220> FEATURE:
<223> OTHER INFORMATION: C1q inhibiting peptide

<400> SEQUENCE: 6

Leu Arg Phe Leu Asn Pro Phe Ser Leu Asp Gly Ser Gly Phe Trp
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: C1q inhibiting peptide

<400> SEQUENCE: 7

Thr Cys Tyr Gly Pro Phe Ser Leu Thr Asn Ser Phe Arg Cys Pro
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: C1q inhibiting peptide

<400> SEQUENCE: 8

Cys Glu Gly Pro Phe Gly Pro Arg His Asp Leu Thr Phe Cys Trp
1               5                   10                  15

<210> SEQ ID NO 9
<211> LENGTH: 12
<212> TYPE: PRT
<213> ORGANISM: Artificial sequence
<220> FEATURE:
<223> OTHER INFORMATION: C1q inhibiting peptide

<400> SEQUENCE: 9

Cys Arg Trp Asp Gly Ser Trp Gly Glu Val Arg Cys
1               5                   10

<210> SEQ ID NO 10
<211> LENGTH: 12
<212> TYPE: PRT
<213> ORGANISM: Artificial sequence
<220> FEATURE:
<223> OTHER INFORMATION: C1q inhibiting peptide

<400> SEQUENCE: 10

Cys Met Trp Val Arg Met Trp Gly Asp Val Asn Cys
1               5                   10

<210> SEQ ID NO 11
<211> LENGTH: 12
<212> TYPE: PRT
<213> ORGANISM: Artificial sequence
<220> FEATURE:
<223> OTHER INFORMATION: C1q inhibiting peptide

<400> SEQUENCE: 11

Cys Phe Trp Ala Gly Lys Phe Gly Leu Gly Thr Cys
1               5                   10

<210> SEQ ID NO 12
<211> LENGTH: 12

```
<212> TYPE: PRT
<213> ORGANISM: Artificial sequence
<220> FEATURE:
<223> OTHER INFORMATION: C1q inhibiting peptide

<400> SEQUENCE: 12

Cys Lys Asp Arg Trp Val Val Glu Glu Arg Cys Cys
1               5                   10

<210> SEQ ID NO 13
<211> LENGTH: 11
<212> TYPE: PRT
<213> ORGANISM: Artificial sequence
<220> FEATURE:
<223> OTHER INFORMATION: C1q inhibiting peptide

<400> SEQUENCE: 13

Cys Trp Asn Arg Phe Lys Lys Met Asp Arg Cys
1               5                   10

<210> SEQ ID NO 14
<211> LENGTH: 16
<212> TYPE: PRT
<213> ORGANISM: Artificial sequence
<220> FEATURE:
<223> OTHER INFORMATION: C1q inhibiting peptide

<400> SEQUENCE: 14

Asn Lys Met Thr Cys Ser Asp Asp Gly Lys Leu Cys Trp Glu His Leu
1               5                   10                  15

<210> SEQ ID NO 15
<211> LENGTH: 30
<212> TYPE: PRT
<213> ORGANISM: Artificial sequence
<220> FEATURE:
<223> OTHER INFORMATION: C1q inhibiting peptide

<400> SEQUENCE: 15

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu Leu
            20                  25                  30

<210> SEQ ID NO 16
<211> LENGTH: 30
<212> TYPE: PRT
<213> ORGANISM: Artificial sequence
<220> FEATURE:
<223> OTHER INFORMATION: C1q inhibiting peptide

<400> SEQUENCE: 16

Asn Pro Val Leu Val Lys Asp Ala Thr Gly Ser Thr Gln Phe Gly Pro
1               5                   10                  15

Val Gln Ala Leu Gly Ala Gln Tyr Ser Met Trp Lys Leu Lys
            20                  25                  30

<210> SEQ ID NO 17
<211> LENGTH: 9
<212> TYPE: PRT
<213> ORGANISM: Artificial sequence
<220> FEATURE:
<223> OTHER INFORMATION: C1q inhibiting peptide

<400> SEQUENCE: 17

Lys Gly Glu Gln Gly Glu Pro Gly Ala
1               5
```

-continued

```
<210> SEQ ID NO 18
<211> LENGTH: 13
<212> TYPE: PRT
<213> ORGANISM: Artificial sequence
<220> FEATURE:
<223> OTHER INFORMATION: C1q inhibiting peptide

<400> SEQUENCE: 18

Ala Gly Arg Pro Gly Arg Arg Gly Arg Pro Gly Leu Lys
1               5                   10

<210> SEQ ID NO 19
<211> LENGTH: 27
<212> TYPE: PRT
<213> ORGANISM: Artificial sequence
<220> FEATURE:
<223> OTHER INFORMATION: C2 and receptor inhibiting peptide

<400> SEQUENCE: 19

Met Ser Pro Ser Leu Val Ser Asp Thr Gln Lys His Glu Arg Gly Ser
1               5                   10                  15

His Glu Val Lys Ile Lys His Phe Ser Pro Tyr
            20                  25

<210> SEQ ID NO 20
<211> LENGTH: 11
<212> TYPE: PRT
<213> ORGANISM: Artificial sequence
<220> FEATURE:
<223> OTHER INFORMATION: C2 and receptor inhibiting peptide

<400> SEQUENCE: 20

His Glu Val Lys Ile Lys His Phe Ser Pro Tyr
1               5                   10

<210> SEQ ID NO 21
<211> LENGTH: 11
<212> TYPE: PRT
<213> ORGANISM: Artificial sequence
<220> FEATURE:
<223> OTHER INFORMATION: C2 and receptor inhibiting peptide

<400> SEQUENCE: 21

Ala Cys Ala His Ile Arg Leu Tyr Ser Cys Arg
1               5                   10

<210> SEQ ID NO 22
<211> LENGTH: 17
<212> TYPE: PRT
<213> ORGANISM: Artificial sequence
<220> FEATURE:
<223> OTHER INFORMATION: peptide that inhibits the C2-C4 interaction

<400> SEQUENCE: 22

Glu Ile Leu Gln Glu Glu Asp Leu Ile Asp Glu Asp Asp Ile Pro Val
1               5                   10                  15

Arg

<210> SEQ ID NO 23
<211> LENGTH: 23
<212> TYPE: DNA
<213> ORGANISM: Artificial sequence
<220> FEATURE:
<222> LOCATION: 876..898
<223> OTHER INFORMATION: human C2 cDNA
```

```
<400> SEQUENCE: 23
ccgccaaccc tactcttatg act                                          23

<210> SEQ ID NO 24
<211> LENGTH: 21
<212> TYPE: RNA
<213> ORGANISM: Artificial sequence
<220> FEATURE:
<223> OTHER INFORMATION: Sense siRNA against nucleotides 876-898 of
      human C2 cDNA

<400> SEQUENCE: 24
gccaacccua cucuuaugau u                                            21

<210> SEQ ID NO 25
<211> LENGTH: 21
<212> TYPE: RNA
<213> ORGANISM: Artificial sequence
<220> FEATURE:
<223> OTHER INFORMATION: Antisense siRNA against nucleotides 876-898 of
      human C2 cDNA

<400> SEQUENCE: 25
ucauaagagu agguuggcu u                                             21

<210> SEQ ID NO 26
<211> LENGTH: 23
<212> TYPE: DNA
<213> ORGANISM: Artificial sequence
<220> FEATURE:
<222> LOCATION: 2436..2458
<223> OTHER INFORMATION: human C2 cDNA

<400> SEQUENCE: 26
gccacgagac tttcacatca atc                                          23

<210> SEQ ID NO 27
<211> LENGTH: 21
<212> TYPE: RNA
<213> ORGANISM: Artificial sequence
<220> FEATURE:
<223> OTHER INFORMATION: Sense siRNA against nucleotides 2436-2458 of
      human C2 cDNA

<400> SEQUENCE: 27
cacgagacuu ucacaucaau u                                            21

<210> SEQ ID NO 28
<211> LENGTH: 21
<212> TYPE: RNA
<213> ORGANISM: Artificial sequence
<220> FEATURE:
<223> OTHER INFORMATION: Antisense siRNA against nucleotides 2436-2458
      of human C2 cDNA

<400> SEQUENCE: 28
uugaugugaa agucucgugu u                                            21

<210> SEQ ID NO 29
<211> LENGTH: 23
<212> TYPE: DNA
<213> ORGANISM: Artificial sequence
<220> FEATURE:
<222> LOCATION: 2435..2457
<223> OTHER INFORMATION: human C2 cDNA (2435-2457)

<400> SEQUENCE: 29
```
cgccacgaga ctttcacatc aat                                              23

<210> SEQ ID NO 30
<211> LENGTH: 21
<212> TYPE: RNA
<213> ORGANISM: Artificial sequence
<220> FEATURE:
<223> OTHER INFORMATION: Sense siRNA against nucleotides 2435-2457 of
      human C2 cDNA

<400> SEQUENCE: 30
ccacgagacu uucacaucau u                                                21

<210> SEQ ID NO 31
<211> LENGTH: 21
<212> TYPE: RNA
<213> ORGANISM: Artificial sequence
<220> FEATURE:
<223> OTHER INFORMATION: Antisense siRNA against nucleotides 2435-2457
      of human C2 cDNA

<400> SEQUENCE: 31
ugaugugaaa gucucguggu u                                                21

<210> SEQ ID NO 32
<211> LENGTH: 23
<212> TYPE: DNA
<213> ORGANISM: Artificial sequence
<220> FEATURE:
<222> LOCATION: 1706..1728
<223> OTHER INFORMATION: human C2 cDNA

<400> SEQUENCE: 32
atgtcactat taagcccaag agc                                              23

<210> SEQ ID NO 33
<211> LENGTH: 21
<212> TYPE: RNA
<213> ORGANISM: Artificial sequence
<220> FEATURE:
<223> OTHER INFORMATION: Sense siRNA against nucleotides 1706-1728 of
      human C2 cDNA

<400> SEQUENCE: 33
gucacuauua agcccaagau u                                                21

<210> SEQ ID NO 34
<211> LENGTH: 21
<212> TYPE: RNA
<213> ORGANISM: Artificial sequence
<220> FEATURE:
<223> OTHER INFORMATION: Antisense siRNA against nucleotides 1706-1728
      of human C2 cDNA

<400> SEQUENCE: 34
ucuugggcuu aauagugacu u                                                21

<210> SEQ ID NO 35
<211> LENGTH: 53
<212> TYPE: PRT
<213> ORGANISM: Artificial sequence
<220> FEATURE:
<223> OTHER INFORMATION: C1r and C1s inhibiting peptide

<400> SEQUENCE: 35

Ile Ala Gly Arg Ser Leu Asn Pro Asn Arg Val Thr Phe Lys Ala Asn
1               5                   10                  15

-continued

```
Arg Pro Phe Leu Val Phe Ile Arg Glu Val Pro Leu Asn Thr Ile Ile
                20              25                  30
Phe Met Gly Arg Val Ala Asn Pro Leu Asn Thr Ile Ile Phe Met Gly
            35              40                  45
Arg Val Ala Asn Pro
    50

<210> SEQ ID NO 36
<211> LENGTH: 51
<212> TYPE: PRT
<213> ORGANISM: Artificial sequence
<220> FEATURE:
<223> OTHER INFORMATION: C1r and C1s inhibiting peptide

<400> SEQUENCE: 36

Phe Leu Glu Ala Ile Pro Met Ser Ile Pro Pro Glu Val Lys Phe Asn
1               5                   10                  15
Lys Pro Phe Tyr Phe Leu Met Ile Glu Gln Asn Thr Lys Ser Pro Leu
                20              25                  30
Phe Met Gly Lys Trp Asn Pro Lys Ser Pro Leu Phe Met Gly Lys Val
            35              40                  45
Val Asn Pro
    50

<210> SEQ ID NO 37
<211> LENGTH: 53
<212> TYPE: PRT
<213> ORGANISM: Artificial sequence
<220> FEATURE:
<223> OTHER INFORMATION: C1r and C1s inhibiting peptide

<400> SEQUENCE: 37

Thr Leu Leu Ser Ala Leu Val Glu Thr Arg Thr Ile Val Arg Phe Asn
1               5                   10                  15
Arg Pro Phe Leu Met Ile Ile Val Pro Pro Asp Thr Gln Asn Ile Phe
                20              25                  30
Asn Ser Lys Val Thr Asn Pro Asp Thr Gln Asn Ile Phe Phe Met Ser
            35              40                  45
Lys Val Thr Asn Pro
    50
```

METHODS AND MATERIALS FOR TREATING AUTOIMMUNE AND/OR COMPLEMENT MEDIATED DISEASES AND CONDITIONS

CROSS-REFERENCE TO RELATED APPLICATIONS

This application is a continuation-in-part application claiming benefit of priority under 35 U.S.C. §120 of pending national stage application U.S. Ser. No. 10/571,379, filed Mar. 20, 2007, now U.S. Pat. No. 7,923,010 which claims benefit of priority under 35 U.S.C. §371 of international application PCT/US2004/029673, filed Sep. 11, 2004, now abandoned, which claims benefit of priority under 35 U.S.C. §119(e) of provisional application U.S. Ser. No. 60/502,086, filed Sep. 11, 2003, now abandoned, the entirety of each application is hereby incorporated by reference.

BACKGROUND OF THE INVENTION

1. Field of the Invention

The present invention is directed to methods and materials for treating autoimmune and/or complement mediated diseases or conditions (in which complement involved either partly or predominantly in pathogenesis) and more particularly, to methods and materials for treating myasthenia gravis.

2. Description of the Related Art

Autoimmune diseases afflict large numbers of individuals in the U.S. and worldwide. For example, Myasthenia gravis ("MG"), an autoimmune neuromuscular disease, afflicts about 60,000 individuals in the United States and about 1,250,000 individuals worldwide. Neuromuscular transmission fails in MG because of decreased sensitivity of the postsynaptic membrane to the neurotransmitter acetylcholine ("ACh"), which results from a loss of acetylcholine receptors ("AChRs") due to a T-cell and B-cell mediated autoimmune attack against the AChR (Christadoss et al., "Immunotherapy for Myasthenia Gravis: a Murine Model," J. Immunol., 136 (7):2437-2440 (1986)). Pemphigus, a group of autoimmune blistering diseases of the skin and/or mucous membranes, afflicts about 12,000 individuals in the United States and about 250,000 individuals worldwide. Autoimmune hemolytic anemia, a condition in which the immune system attacks the red blood cells, resulting in fewer of these oxygen-transporting cells, afflicts about 12,000 individuals in the United States and about 280,000 individuals worldwide. Idiopathic thrombocytopenic purpura, a bleeding disorder characterized by the destruction of platelets by the immune system, resulting in too few platelets in the blood, afflicts about 12,000 individuals in the United States and about 250,000 individuals worldwide. Autoimmune glomerulonephritis, a nephritis which is accompanied by inflammation of the capillary loops in the glomeruli of the kidney, afflicts about 60,000 individuals in the United States and over a million individuals worldwide.

Still other examples of autoimmune diseases that afflict large numbers of individuals in the U.S. and worldwide include Type I diabetes, rheumatoid arthritis, Hashimoto's disease, Graves disease, dermatomyositis, autoimmune vitiligo, psoriasis, and Guillain-Barre syndrome.

At present, many autoimmune diseases are treated using non-specific immunosuppressive drugs, such as steroids. However, steroids can have long-term side-effects, and they can suppress desirable immune responses. Non-steroidal immunosuppressive drugs have also been developed. For example, Eculizumab is a humanized monoclonal antibody that prevents the cleavage of human complement component C5 into pro-inflammatory components, and it has been approved to treat rheumatoid arthritis, nephritis, and phemphigus. However, use of this monoclonal antibody must be carefully monitored, as it can reduce a patient's ability to clear viruses, bacteria, and apoptotic and tumor cells, thus making patients more susceptible to bacterial and viral infection.

In view of the above, a need remains for methods and materials for treating autoimmune diseases. The present invention is directed, in part, to addressing this need.

SUMMARY OF THE INVENTION

The present invention relates to a method for treating an autoimmune disease or condition in a subject. The method includes administering to the subject a compound which inhibits the subject's classical complement pathway.

The present invention also relates to a method for suppressing transplant rejection in particular hyperacute graft rejection and kidney reperfusion injury in a subject. The method includes administering to the subject a compound which inhibits the subject's classical complement pathway.

The present invention also relates to a composition which a pharmaceutically acceptable excipient and a specific inhibitor of one of the following targets: C1q, C1r, C1s, C2 or C4.

The present invention also relates to a composition which includes a specific inhibitor that inhibits the interaction between C2 and C4 and a pharmaceutically acceptable excipient.

BRIEF DESCRIPTION OF THE DRAWINGS

FIGS. 2A-2B are bar graphs showing serum C1q-circulating immune complex ("CIC") levels (FIG. 2A) and serum C3 levels (FIG. 2B) in various mice. FIG. 2C is a graph showing experimental autoimmune myasthenia gravis ("EAMG") severity as a function of serum CIC levels in RIIIS/J mice.

FIG. 5A shows the anti-AChR IgG levels (determined by RIA); FIG. 5B shows the anti-AChR IgG1 levels (determined by ELISA); FIG. 5C shows the anti-AChR IgG2b levels (determined by ELISA); and FIG. 5D shows the total IgG levels (determined by ELISA).

FIGS. 6A-6D are images of frozen muscle sections of $C3^{+/+}$ (FIG. 6A), $C4^{+/+}$ (FIG. 6B), $C3^{-/-}$ (FIG. 6C), and $C4^{-/-}$ (FIG. 6D) mice double-stained with .alpha.-bungarotoxin (".alpha.-BTx") (which binds to neuromuscular junction ("NMJ")) and antibodies directed against either IgG, C3, or membrane attack complex, C5b-C9 ("MAC").

(FIG. 8D)) of anti-C1q-treated mice and control IgG-treated mice.

FIGS. 10A-10C are bar graphs and images showing the results of flow cytometry analysis of the lymph node cells and immunohistochemistry performed on paraffin-embedded spleen sections of anti-C1q-treated mice and control IgG-treated mice.

FIGS. 12A-12F are bar graphs showing serum anti-AChR levels in anti-C1q-treated mice and control IgG-treated mice.

FIG. 14 is a graph showing average grip strengths of mice afflicted with ongoing EAMG while being treated with anti-C1q or control IgG at various times during the treatment period.

FIG. 18 is a bar graph showing grip strength analysis of AChR immunized mice treated with C2 siRNA.

FIG. 19A-19D are bar graphs showing serum anti-AChR IgM and IgG isotypes in C2 siRNA treated EAMG mice.

FIG. 21 is a bar graph showing lack of weight loss in siRNA treated mice.

FIG. 24 is a bar graph showing C2 siRNA treatment prevents AChR degradation following AChR immunization.

DETAILED DESCRIPTION OF THE INVENTION

Figure 1:
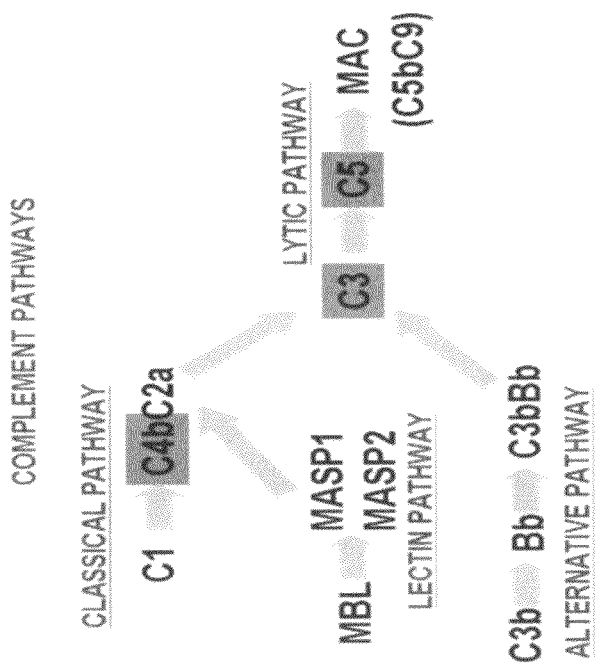
FIG. 1 is a graphic illustrating three separate complement pathways (classical, mannose binding lectin ("MBL"), and alternative pathways) and the complement components of each of the pathways.

One aspect of the present invention relates to a method for treating an autoimmune disease or condition in a subject. The method includes administering to the subject a compound which inhibits the subject's classical complement pathway.

Another aspect of the present invention relates to a method for suppressing hyperacute graft rejection in a subject. The method includes administering to the subject a compound which inhibits the subject's classical complement pathway.

As used herein, "autoimmune disease or condition" is meant to refer to a disease or condition which results from or is exacerbated by the body's immune system attack on its own cells, tissues, organs, and/or systems, for example those of the blood, the digestive tract, the eyes, the glands, the heart, the joints, the kidneys, the lungs, the muscles, the nerves, the brain, the connective tissue, and the skin. Examples of such autoimmune diseases or conditions include those in which the complement plays a role in disease pathogenesis, such as Type I diabetes, atherosclerosis, rheumatoid arthritis, Hashimoto's disease, Graves disease, dermatomyositis, autoimmune vitiligo, psoriasis, Guillain-Barre syndrome, paroxysmal nocturnal hemoglobinuria, ulcerative colitis, Crohn's disease, Coeliac disease, and Kawasaki syndrome. Other examples include antibody dependent complement mediated autoimmune diseases, such as myasthenia gravis, pemphigus, autoimmune hemolytic anemia, idiopathic thrombocytopenic purpura, autoimmune glomerulonephritis (e.g., autoimmune forms of membranoproliferative glomerulonephritis), and anti-glomerular basement membrane nephritis.

"Treatment" as used herein, is meant to refer to both therapeutic treatments (for example, as in the case where the subject already shows one or more clinical signs of the autoimmune disease or condition), as well as to preventative treatments (for example, as in the case where the subject does not show any clinical signs of the autoimmune disease or condition and during remissions of the disease or condition). In the former case, therapeutic treatment can be carried out to stop or impede progression of the disease or condition, or to reverse its progression, or to stop, impede, or reverse one or more symptoms or other manifestations of the disease or condition. In the latter case, preventative treatment can be carried out to reduce the risk that the subject will develop the disease or condition or one or more symptoms or other manifestations of the disease or condition or to prevent or otherwise reduce the risk of relapse of the disease or condition.

"Suppressing", as used herein in the context of hyperacute graft rejection, is meant to refer to any quantitatively or qualitatively measurable or observable reduction in hyperacute graft rejection of, for example, a tissue graft of an organ, such as of a kidney, a liver, a lung, a heart, skin and/or an eye.

"Subject", as used herein, is meant to include mammals, such as mice, rats, cats, dogs, monkeys, bovine, porcine, equine, and humans. Suitable human subjects include, for example, those who have previously been diagnosed as being afflicted with a particular autoimmune disease or condition (such as any one or more of those described above); those who have previously been determined to be at risk of developing a particular autoimmune disease or condition (such as any one or more of those described above); those who have not previously been diagnosed as being afflicted with a particular autoimmune disease or condition (such as any one or more of those described above); and/or those who have not previously been determined to be at risk of developing a particular autoimmune disease or condition (such as any one or more of those described above). Other suitable human subjects include, for example, those who have recently undergone a grafting procedure, as well as those who are about to undergo a grafting procedure.

As discussed above, the method includes administering to the subject a compound which inhibits the subject's classical complement pathway. The inhibition can be direct or indirect, and it can be selective or non-selective. As used herein, classical complement pathway inhibition is to be deemed to be "selective" when at least one other pathway to complement activation (e.g., the MBL pathway and/or the alternative pathway) is not substantially inhibited (e.g., inhibited by less than about 50%, such as by less than about 40%, by less than about 30%, by less than about 20%, by less than about 10%, etc.). Inhibition of the classical complement pathway can be specific, as in the case where both the MBL pathway and the alternative pathway are not substantially inhibited (e.g., inhibited by less than about 50%, such as by less than about 40%, by less than about 30%, by less than about 20%, by less than about 10%, etc.).

Inhibition of the classical complement pathway can be carried out, for example, by using a compound that inhibits C1q, C2, and/or C4 complement proteins. In one embodiment, the compound inhibits the subject's classical complement pathway by selectively inhibiting C1q. As used herein, a compound is to be deemed to "selectively" inhibit C1q when at least one of the other components in the classical complement pathway (e.g., C2 and/or C4) is not substantially inhibited by the compound (e.g., inhibited by less than about 50%, such as by less than about 40%, by less than about 30%, by less than about 20%, by less than about 10%, etc.). In another embodiment, the compound inhibits the subject's classical complement pathway by selectively inhibiting C2. As used herein, a compound is to be deemed to "selectively" inhibit C2 when at least one of the other components in the classical complement pathway (e.g., C1q and/or C4) is not substantially inhibited by the compound (e.g., inhibited by less than about 50%, such as by less than about 40%, by less than about 30%, by less than about 20%, by less than about 10%, etc.). In yet another embodiment, the compound inhibits the subject's classical complement pathway by selectively inhibiting C4. As used herein, a compound is to be deemed to "selectively" inhibit C4 when at least one of the other components in the classical complement pathway (e.g., C1q and/or C2) is not substantially inhibited by the compound (e.g., inhibited by less than about 50%, such as by less than about 40%, by less than about 30%, by less than about 20%, by less than about 10%, etc.).

The compound can be a specific inhibitor of C1q. In this regard, a compound is to be deemed to be a "specific" inhibitor of C1q when the compound inhibits C1q; does not substantially inhibit C2 and/or C4; and does not substantially inhibit the MBL pathway and/or the alternative pathway. Alternatively, the compound can be a specific inhibitor of C2. In this regard, a compound is to be deemed to be a "specific" inhibitor of C2 when the compound inhibits C2; does not substantially inhibit C1q and/or C4; and does not substantially inhibit the MBL pathway and/or the alternative pathway. Still alternatively, the compound can be a specific inhibitor of C4. In this regard, a compound is to be deemed to be a "specific" inhibitor of C4 when the compound inhibits C4; does not substantially inhibit C1q and/or C2; and does not substantially inhibit the MBL pathway and/or the alternative pathway.

Inhibition of C2 or C4 will inhibit the MBL pathway, but not the alternative pathway. MBL pathway is not involved in MG pathogenesis (ref. Li, J., Qi H., Tüzün E., Allman W., Yilmaz V., Saini S. S., Deymeer F., Saruhan-Direskeneli G., Christadoss, P. Mannose-binding lectin pathway is not involved in myasthenia gravis pathogenesis. J. Neuroimmunol. 2009, 208:40-5. PMID: 19193448). Therefore, C2 or C4 inhibition will treat MG via inhibition of the classical pathway.

Examples of compounds that can be used in the practice of the methods of the present invention include anti-C1q antibodies, anti-C2 antibodies, and anti-C4 antibodies. These antibodies can be monoclonal or polyclonal, and, depending on the subject to whom they are to be administered, they can be chimeric. For example, where the subject is a human, chimeric humanized anti-C1q antibodies can be employed; chimeric humanized anti-C2 antibodies can be employed; or chimeric humanized anti-C4 antibodies can be employed.

The aforementioned anti-C1q antibodies, anti-C2 antibodies, and anti-C4 antibodies can be prepared by conventional methods. Monoclonal antibodies that bind to C1q, C2, or C4 can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibodies are well known in the art. See, e.g., Campbell, Monoclonal Antibody Technology: Laboratory Techniques in Biochemistry and Molecular Biology, Amsterdam, The Netherlands: Elsevier Science Publishers (1984) ("Campbell"); and St. Groth et al., J. Immunol. Methods., 35:1-21 (1980), which are hereby incorporated by reference. Any animal (mouse, rabbit, etc.) which is known to produce antibodies can be immunized with the antigenic material C1q, C2, C4, combinations thereof, or an antigenic fragment thereof. Methods for immunization are well known in the art. Such methods include subcutaneous or intraperitoneal injection of the antigenic material. One skilled in the art will recognize that the amount of antigenic material used for immunization will vary based on the animal which is immunized, the antigenicity of the antigenic material, and the site of injection.

The antigenic material (C1q, C2, C4, combinations thereof, or an antigenic fragment thereof) which is used as an immunogen may be modified or administered in an adjuvant in order to increase the antigenic materials antigenicity. Methods of increasing the antigenicity of an antigenic material are well known in the art and include, but are not limited to, coupling the antigen with a heterologous protein (such as a globulin or beta-galactosidase) or including an adjuvant during immunization. For monoclonal antibodies, spleen cells from the immunized animals are removed, fused with myeloma cells, such as SP2/O—Ag 15 myeloma cells, and allowed to become monoclonal-antibody-producing hybridoma cells.

Any one of a number of methods well known in the art can be used to identify the hybridoma cell which produces an antibody with the desired characteristics. These include screening the hybridomas using, for example, an ELISA assay, a western blot analysis, or a radioimmunoassay. See, e.g., Lutz et al., Exp. Cell Res., 175:109-124 (1988), which is hereby incorporated by reference. Hybridomas secreting the desired antibodies are cloned, and the class and subclass are determined using procedures known in the art, such as those set described in Campbell, which is hereby incorporated by reference. For polyclonal antibodies, antibody containing antisera is isolated from the immunized animal and is screened for the presence of antibodies with the desired specificity using one of the above-described procedures.

"Antibodies", as used herein are meant to include antibody fragments, such as Fab, Fab2, and Fc fragments, as well as humanized forms. Humanized forms of the antibodies can be generated using one of the procedures known in the art, such as chimerization. Such methods are described, for example, in U.S. Pat. No. 4,816,567 to Cabilly et al.; Mage et al., pp. 79-97 in Monoclonal Antibody Production Techniques and Applications, New York: Marcel Dekker, Inc. (1987); Jones et al., Nature, 321:522-525 (1986); Reichmann et al., Nature, 332:323-329 (1988); and Presta, Curr. Op. Struct. Biol., 2:593-596 (1992); Perisic et al., Structure, 2:1217-1226 (1994); Pei et al., PNAS, 94:9637-9642 (1997); Hollinger et al., Protein Engineering, 9:299-305 (1996); and Millstein et al., Nature, 305:537-539 (1983); which are hereby incorporated by reference.

Antigenic C1q can be prepared, for example, using the methods described in Yonemasu et al., "Purification and Characterization of Subcomponent C1q of the First Component of Bovine Complement," J. Biochem., 88:1545-1554 (1980), which is hereby incorporated by reference. Antigenic C4 can be prepared, for example, using the methods described in Reilly et al., Journal of Immunology, 147(9):3018-3023 (1991) and Kozlov et al., Biokhimiia, 51(5):707-718 (1986), which are hereby incorporated by reference. Alternatively, the aforementioned antigenic C1q, C2, and C4 proteins can be obtained from commercial sources or other sources. For example, antigenic C1q and C4 proteins can be obtained from Quidel Corporation (San Diego, Calif.).

Alternatively, the aforementioned anti-C1q antibodies, anti-C2 antibodies, and anti-C4 antibodies can be obtained from commercial sources or other sources. For example, monoclonal and polyclonal anti-C1q and C4 can be obtained from Quidel Corporation (San Diego, Calif.).

Still alternatively, the aforementioned anti-C1q antibodies, anti-C2 antibodies, and anti-C4 antibodies can be produced from hybridoma cell lines available from the ATCC. For example, anti-C1q monoclonal antibodies can be produced from hybridoma cell line 4A4B11, which is available from the American Type Culture Collection ("ATCC") (Manassas, Va.) (ATCC No. HB-8327, which is hereby incorporated by reference); or the anti-C1q monoclonal antibodies can be produced from hybridoma cell line 12A5B7, which is available from the ATCC (ATCC No. HB-8328, which is hereby incorporated by reference). Anti-C2/C2a monoclonal antibodies can be produced from a hybridoma cell line that is available from the ATCC (ATCC No. PTA-1553, which is hereby incorporated by reference).

Examples of other compounds that inhibit the subject's classical complement pathway which can be used in the practice of methods of the present invention include synthetic peptide inhibitors of C1q, C2, and/or C4. As discussed above, these synthetic peptide inhibitors can be selective (e.g., to C1q) and/or specific (e.g., to C1q). Synthetic peptide inhibitors of C1q, C2, or C4 can be prepared by selecting peptide sequences from various phage-displayed peptide libraries on the basis of phage binding to C1q, C2, or C4, respectively. The following peptide inhibitors of complement pathway can be obtained using the methods described in references incorporated herein. C1q inhibiting peptides, listed in Table 1 as SEQ ID:1-3, can be obtained according to Takada et al., Immunopharmacology. 1985 April; 9(2):87-95, which is hereby incorporated by reference. A C1q inhibiting peptide, listed in Table 1 as SEQ ID:4, can be obtained according to Ghebrehiwet et al., J Exp Med. 1994 Jun. 1; 179(6):1809-21, which is hereby incorporated by reference. A C1q inhibiting peptide, listed in Table 1 as SEQ ID:5, can be obtained according to Fryer et al., Transplantation, 2000 Sep. 15; 70(5):828-36, which is hereby incorporated by reference. C1q inhibiting peptides, listed in Table 1 as SEQ ID:6-14, can be obtained according to Roos et al., J. Immunol. 2001 Dec. 15; 167(12):7052-9, which is hereby incorporated by reference. C1q inhibiting peptides, listed in Table. 1 as SEQ ID:15-16, can be obtained according to Gronemus et al., Mol Immunol. 2010 November-December; 48(1-3):305-13, which is hereby incorporated by reference. A C1q inhibiting peptide, listed in Table. 1 as SEQ ID:17, can be obtained according to Trinder et al., Scand J Immunol. 1999 December; 50(6):635-41, which is hereby incorporated by reference. A C1q inhibiting peptide, listed in Table 1 as SEQ ID:18, can be obtained according to Bradley et al., Biochim Biophys Acta. 1999 Apr. 14; 1418(1):19-30, which is hereby incorporated by reference. C1q inhibiting peptides, purified C1 esterase inhibitors from human plasma, can be obtained as a pharmaceutical composition as CINRYZE (which is FDA-approved to be used for hereditary angioedema) from ViroPharma Incorporated.

C2 and receptor inhibiting peptides, listed in Table. 1 as SEQ ID Nos:19-20, can be obtained according to Inal et al., "A Schistosoma protein, Sh-TOR, is a novel inhibitor of complement which binds human C2," FEBS Lett. 2000 Mar. 24; 470(2):131-4, and Inal et al., J. Immunol. 2005 Jan. 1; 174(1):356-66, which are hereby incorporated by reference. A C2 inhibiting peptide, listed in Table 1 as SEQ ID:21, can be obtained according to Kadam et al., J. Immunol., 2010 Jun. 15; 184(12):7116-24, which is hereby incorporated by reference. A peptide that inhibits the interaction between C2 and C4, listed in Table 1 as SEQ ID:22, can be obtained according to Pan et al., J. Immunol. 2000 Sep. 1; 165(5):2518-27, which is hereby incorporated by reference. C1r and C1s inhibiting peptides, listed in Table. 1 as SEQ ID:35-37, can be obtained according to Glover et al., Mol Immunol. 1988 December; 25(12):1261-7, which is hereby incorporated by reference.

TABLE 1

| SEQ ID | Peptide Sequence |
|---|---|
| 1 | WYVDG |
| 2 | TKPR |
| 3 | GKEYK |
| 4 | LHTDGDKAFVDFLSDEIKEERKIQ |
| 5 | LEQGENVFLQATLL |
| 6 | LRFLNPFSLDGSGFW |
| 7 | TCYGPFSLTNSFRCP |
| 8 | CEGPFGPRHDLTFCW |
| 9 | CRWDGSWGEVRC |
| 10 | CMWVRMWGDVNC |
| 11 | CFWAGKFGLGTC |
| 12 | CKDRWVVEERCC |
| 13 | CWNRFKKMDRC |
| 14 | NKMTCSDDGKLCWEHL |
| 15 | PAICQRATATLGTVGSNTSGTTEIEACILL |
| 16 | NPVLVKDATGSTQFGPVQALGAQYSMWKLK |
| 17 | KGEQGEPGA |
| 18 | AGRPGRRGRPGLK |
| 19 | MSPSLVSDTQKHERGSHEVKIKHFSPY |
| 20 | HEVKIKHFSPY |
| 21 | ACAHIRLYSCR |
| 22 | EILQEEDLIDEDDIPVR |
| 35 | IAGRSLNPNRVTFKANRPFLVFIREVPLNTIIFMGRVANPLNTIIFMGRVANP |
| 36 | FLEAIPMSIPPEVKFNKPFYFLMIEQNTKSPLFMGKWNPKSPLFMGKVVNP |
| 37 | TLLSALVETRTIVRFNRPFLMIIVPPDTQNIFNSKVTNPDTQNIFFMSKVTNP |

Examples of still other compounds that inhibit the subject's classical complement pathway which can be used in the practice of methods of the present invention include those which inhibit macrophage C1q secretion. Examples of such compounds include 3,4-dehydro-DL-proline ("DHP") and 2,2'-dipyridyl. Other examples of compounds that can be used in the practice of the methods of the present invention include C1q small interfering RNAs (siRNAs), C2 siRNAs, and C4 siRNAs.

In general, techniques for preparing siRNAs against a given gene target are well known in the art. The aforementioned C1q siRNAs, C2 siRNAs, and C4 siRNAs can be prepared by conventional methods. Any one of a number of methods well known in the art can be used to prepare siRNAs with the desired characteristics.

The siRNAs can be designed, for example, through the use of software such as BIOPREDsi, siDirect, siRNA Design etc. In order to select potent siRNA, an algorithm based on criteria such as low GC content, lack of inverted repeats etc. can be applied. Selected siRNA should also have the least or no off-target effect. As an example, human C2 siRNAs for clinical trial could be derived from the human C2 cDNA sequence (Genbank Accession NM_000063), said cDNA sequences comprise sequences listed in Table 2 as SEQ ID:23, SEQ ID:26, SEQ ID: 29., and SEQ ID: 32. Accordingly, human C2 siRNAs, listed in Table 2 and SEQUENCE LISTING as SEQ ID:24-25, can be developed to target cDNA sequence SEQ ID:23; human C2 siRNAs, listed in Table 2 as SEQ ID:27-28, can be developed to target cDNA sequence SEQ ID:26; human C2 siRNAs, listed in Table 2 as SEQ ID:30-31, can be developed to target cDNA sequence SEQ ID:29; human C2 siRNAs, listed in Table 2 as SEQ ID:33-34, can be developed to target cDNA sequence SEQ ID:32. Alternatively, the aforementioned C1q siRNAs, C2 siRNAs, and C4 siRNAs can be obtained from commercial sources or other sources.

TABLE 2

| SEQ ID | Note | Nucleotide Sequence from 5' to 3' |
|---|---|---|
| 23 | cDNA (876-898) | CC GCCAACCCTACTCTTATGA CT |
| 24 | Sense siRNA | GCCAACCCUACUCUUAUGA UU |
| 25 | Antisense siRNA | UCAUAAGAGUAGGGUUGGC UU |
| 26 | cDNA (2436-2458) | GC CACGAGACTTTCACATCAA TC |
| 27 | Sense siRNA | CACGAGACUUUCACAUCAA UU |
| 28 | Antisense siRNA | UUGAUGUGAAAGUCUCGUG UU |
| 29 | cDNA (2435-2457) | CG CCACGAGACTTTCACATCA AT |
| 30 | Sense siRNA | CCACGAGACUUUCACAUCA UU |
| 31 | Antisense siRNA | UGAUGUGAAAGUCUCGUGG UU |
| 32 | cDNA (1706-1728) | AT GTCACTATTAAGCCCAAGA GC |
| 33 | Sense siRNA | GUCACUAUUAAGCCCAAGA UU |
| 34 | Antisense siRNA | UCUUGGGCUUAAUAGUGAC UU |

The aforementioned antibodies and other compounds can be administered to the subject by any conventional route, and they can be made up in any suitable dosage form appropriate for the desired use. Examples of suitable dosage forms include oral, or topical dosage forms or dosage forms suitable for parenteral administration include solutions, suspensions, dispersions, emulsions, conjugated to polymer or in plasmid containing vector and the like.

Illustratively, suitable dosage forms for oral use include tablets, dispersible powders, granules, capsules, suspensions, syrups, and elixirs. Inert diluents, carriers, and other excipients for tablets include, for example, calcium carbonate, sodium carbonate, lactose, and talc. Tablets may also contain other excipients, such as granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents, carriers, and other excipients which may be used in capsules include, for example, calcium carbonate, calcium phosphate, and kaolin. Suspensions, syrups, and elixirs may contain conventional excipients, for example, methyl cellulose, tragacanth, sodium alginate, wetting agents (such as lecithin and polyoxyethylene stearate), and preservatives (such as ethyl-p-hydroxybenzoate).

Dosage forms suitable for parenteral administration include solutions, suspensions, dispersions, emulsions, and the like. They may also be manufactured in the form of solid compositions which can be dissolved or suspended in sterile injectable medium immediately before use. They may contain suspending or dispersing agents or other excipients known in the art. Examples of parenteral administration are intraventricular, intracerebral, intramuscular, intravenous (including infusion), intraperitoneal, rectal, and subcutaneous administration.

In addition to the above, generally non-active components of the above-described formulations, these formulations can include other active materials, for example, actives which have been identified as useful in the treatment of autoimmune disorders or conditions or in the alleviation of symptoms associated therewith. These actives can be broad-based actives, such as those that are useful in the treatment of a variety of autoimmune disorders or conditions or in the alleviation of symptoms associated with a variety of autoimmune disorders or conditions; or they may be more specific, for example, as in the case where the other active is specific for the treatment of the particular autoimmune disorder or condition with which the subject is afflicted or for the alleviation of symptoms associated with the particular autoimmune disorder or condition. As further illustration of the actives which can be additionally included in the above-described formulations (i.e., in addition to the antibodies and other compounds and in addition to non-active components), there can be mentioned actives which are conventionally employed to suppress other types of graft rejection (i.e., other than hyperacute graft rejection).

It will be appreciated that the actual preferred amount of compound to be administered according to the present invention will vary according to the particular compound, the particular composition formulated, and the mode of administration. Many factors that may modify the action of the compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

The present invention, in yet another aspect thereof, relates to a composition that includes a specific inhibitor of the classical complement pathway and a pharmaceutically acceptable excipient. Examples of suitable specific inhibitors include anti-C1q antibodies, anti-C2 antibodies, anti-C4 antibodies, C1q inhibiting peptides, C1r inhibiting peptides, C1s inhibiting peptides, C2 inhibiting peptides, C4 inhibiting peptides, and peptides that inhibit C2-C4 interaction. These antibodies or peptides can be prepared by the methods described hereinabove, or they can be obtained commercially or from other sources. These antibodies or peptides used in the compositions of the present invention can be prepared, for example, in accordance with the methods discussed hereinabove. The composition of the present invention further includes (i.e., in addition to the specific inhibitor) a pharmaceutically acceptable excipient. Examples of suitable pharmaceutically acceptable excipients include sterile liquid pharmaceutically acceptable carriers and diluents, non-sterile liquid pharmaceutically acceptable carriers and diluents, sterile solid pharmaceutically acceptable carriers and diluents, and non-sterile solid pharmaceutically acceptable carriers and diluents. Other suitable pharmaceutically acceptable excipients which can be used in the compositions of the present invention include those discussed above with regard to dosage forms. Excipients further include C2siRNA conjugaton to a polymer, C2 siRNA inserted in to liposomes or in to plasmid containing vectors for in vivo delivery, one could make C2siRNA-polymer complex for in vivo delivery (TransIT In vivo polymer solution, Cat #MIR 5100 could be obtained from Mirus Biocorp and C2siRNA-polymer complex can be prepared as per manufacturer's protocol).

The present invention, in yet another aspect thereof, relates to a composition that includes an siRNA against C1q, or C2, or C4 and a pharmaceutically acceptable excipient. These siRNAs can be prepared by the methods described hereinabove, or they can be obtained commercially or from other sources. These siRNAs used in the compositions of the present invention can be a human C1q, or C2, or C4 siRNA, prepared, for example, in accordance with the methods discussed hereinabove. The composition of the present invention further includes (i.e., in addition to the siRNA) a pharmaceutically acceptable excipient. Examples of suitable pharmaceutically acceptable excipients include sterile liquid pharmaceutically acceptable carriers and diluents, non-sterile liquid pharmaceutically acceptable carriers and diluents, sterile solid pharmaceutically acceptable carriers and diluents, and non-sterile solid pharmaceutically acceptable carriers and diluents. Other suitable pharmaceutically acceptable excipients which can be used in the compositions of the present invention include those discussed above with regard to dosage forms.

The present invention is further illustrated with the following examples.

EXAMPLE 1

Overview of the Examples, MG, EAMG, the Complement System, and the Role of Complements in MG and EAMG To delineate the importance of the classical and lytic complement pathways in experimental autoimmune myasthenia gravis ("EAMG") pathogenesis, EAMG was induced in C3 or C4 gene knockout ("KO") mice with acetylcholine receptor (AChR) immunization and observed that these strains of mice were highly resistant to EAMG induction. Secondly, EAMG prevention experiments were performed on wild-type C57BL/6 (B6) mice using anti-C1q antibodies ("anti-C1q") and this treatment efficiently prevented the induction of EAMG. Examination of immunological parameters revealed that neither C4 KO mice nor anti-C1q treated mice developed prominent immunodeficiency. Thus, these studies show that anti-C1q treatment barely interferes with very few of the immunological factors and does not cause prominent immunodeficiency, but still prevents the generation of EAMG. Further, EAMG prevention experiments were performed on wild-type C57BL/6 (B6) mice using C2 siRNAs and this treatment efficiently prevented the induction of EAMG.

Neuromuscular transmission fails in MG because of decreased sensitivity of the postsynaptic membrane to the neurotransmitter acetylcholine (ACh), which results from a loss of acetylcholine receptors (AChRs) due to a T-cell and B-cell mediated autoimmune attack against the AChR (Christadoss et al., J. Immunol., 136(7):2437-2440 (1986), which is hereby incorporated by reference). An experimental model of MG (EAMG) can be induced in several mammalian species by inoculation of small quantities of electric organ AChR of electric rays (Torpedo californica) in adjuvants.

Anti-AChR antibodies are found in about 90% of MG patients, and these antibodies, together with complements (activated by antibody-AChR complex), are implicated as major constituents of the pathogenetic events leading to neuromuscular junction ("NMJ") destruction in both MG and EAMG. Antibodies are suggested to take part in functional AChR loss by blocking AChR, by increasing AChR endocytosis, or by activating the complement-mediated inflammatory destruction of NMJ (Sahashi et al., J. Neuropathol. Exp. Neurol., 37(2):212-223 (1978), which is hereby incorporated by reference). However, their serum levels are not correlated with the clinical severity of disease in both MG and EAMG (Nicholson et al., Clin. Exp. Neurol., 18:61-69 (1981, which is hereby incorporated by reference). This suggests that there may be other critical factors (e.g. complements, cytokines), which contribute to MG and EAMG induction.

The complement system is part of the innate immune system and consists of many proteins that act as a cascade, where each enzyme acts as a catalyst for the next. The complement system is illustrated in FIG. 1. In FIG. 1, grey solid boxes associated with complement factors C4b, C3, and C5 indicate that the importance of these complement factors. As FIG. 1 illustrates, activation of the complement cascade is launched via three separate complement pathways (classical, mannose binding lectin ("MBL"), and alternative pathways). Predominantly, classical pathway is activated by immune complexes, whereas the other two pathways are activated by various pathogens as well as tumor cells, bacterial products, etc. All pathways merge in the lytic pathway, and, irrespective of which pathway is activated, C3 is finally triggered to initiate the activation cascade of lytic pathway that ends with the formation of a membrane attack complex ("MAC").

The proposition that anti-AChR antibodies destroy AChRs located at the NMJ via the complement system is based upon the observation that IgG, C3, and MAC are co-localized at the NMJs of MG patients (Engel et al., Mayo Clin. Proc., 52(5): 267-280 (1977); and Tsujihata et al., Neurology, 39(10): 1359-1363 (1989), which are hereby incorporated by reference). So, plausibly, anti-AChR antibodies activate the complement cascade (possibly the classical pathway since this is activated by immune complexes) to induce MAC, which eventually destroys the NMJ. There is substantial evidence that complements play a very important role in the immunopathogenesis of EAMG. C5 deficiency in mice can prevent EAMG development (Christadoss, J. Immunol., 140 (8):2589-2592 (1988), which is hereby incorporated by reference); and inhibition of C3 by cobra venom factor inhibits disease induction. Collectively, these reports show that, at least in the murine model of MG, activation of MAC by the complement system is imperative for muscle AChR loss and, thus, for MG induction.

EXAMPLE 2

Severity of EAMG in RIIIS/J Mice is Associated with Increased Production of C1q-Conjugated Immune Complexes and C3

A mouse strain called RIIIS/J was used to explore the factors that might be related with increased susceptibility to MG in this strain. RIIIS/J mice, B10.RIII mice (having the same MHC haplotype H-2r), F1 mice (produced by crossing RIIIS/J and B10.RIII mice), and B6 mice (as a control) were immunized with AChR. Among all these strains of mice, RIIIS/J mice had significantly earlier EAMG onset and higher incidence and severity of EAMG (Tuzun et al., J. Immunol., 172(9):5743-5752 (2004), which is hereby incorporated by reference).

Although functioning of MHC molecules are imperative for EAMG induction, and, thus, EAMG in RIIIS/J mice should be associated with MHC molecules, increased EAMG incidence and severity of RIIIS/J mice may be associated with a non-MHC factor(s) as well since B10.RIII mice (having comparable incidence and severity to B6 mice and lower incidence and severity as compared to RIIIS/J mice) share the same MHC haplotype with RIIIS/J mice.

Among other factors, increased EAMG incidence and severity of RIIIS/J mice were associated with increased CD4+ lymph node cell counts and elevated serum C3 and C1q-conjugated immune complex ("C1q-CIC") levels, as shown in FIGS. 2A and 2B. Moreover, serum C1q-CIC levels were significantly correlated with the clinical severity of EAMG in RIIIS/J mice, as shown in FIG. 2C.

Figure 3:
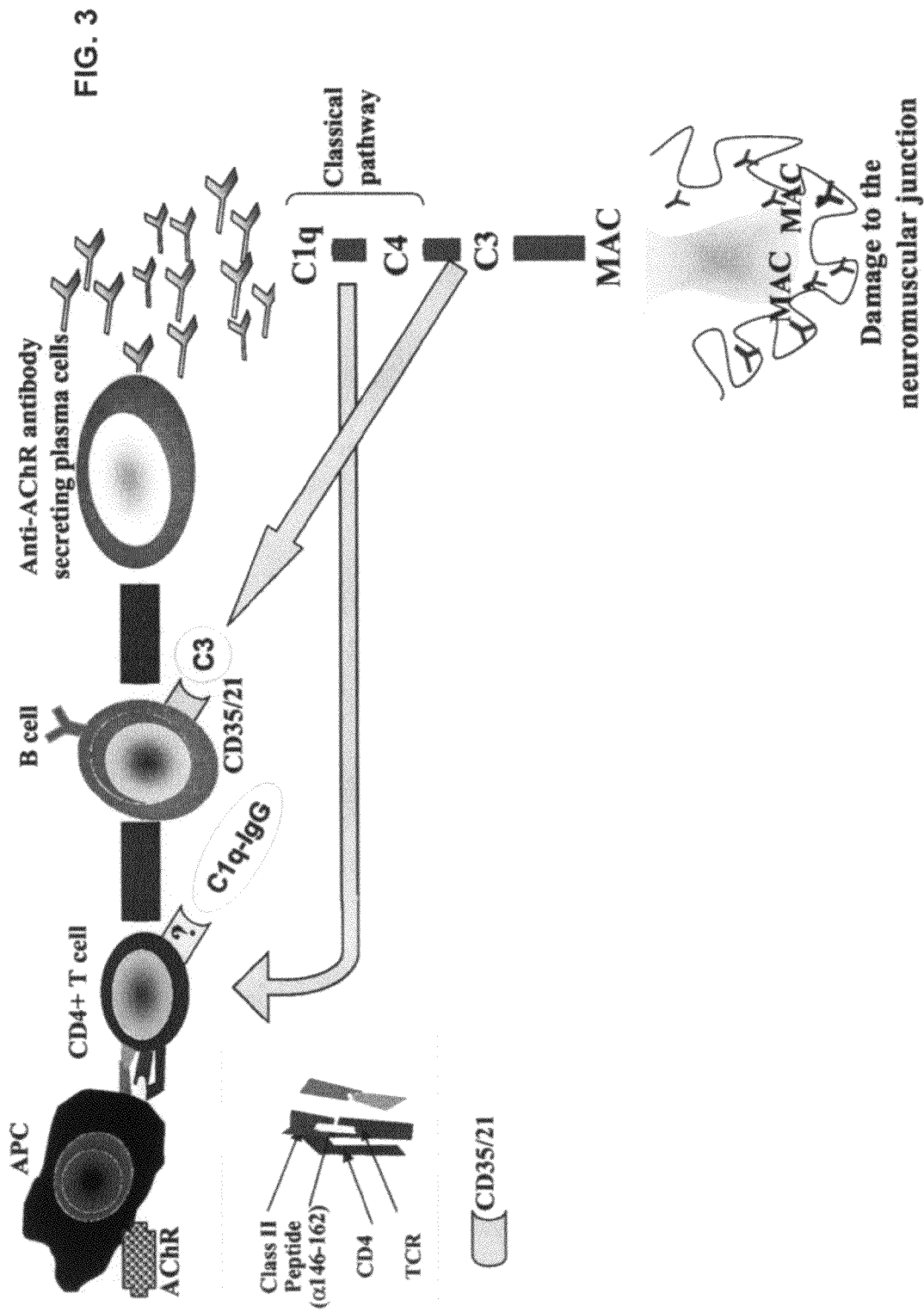
FIG. 3 is a graphic illustrating a hypothetical mechanism of EAMG immunopathogenesis.
Figure 4A:
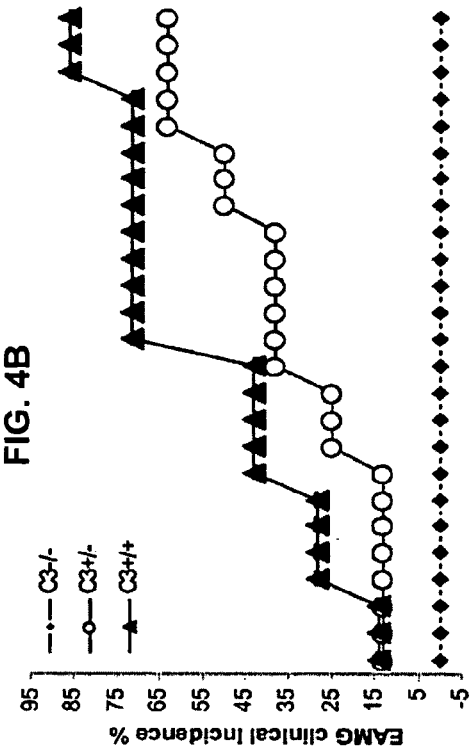
FIGS. 4A and 4B are graphs showing the effect of C3 gene deletion on clinical EAMG development in terms of EAMG severity (FIG. 4A) and EAMG incidence (FIG. 4B).
Figure 4B:
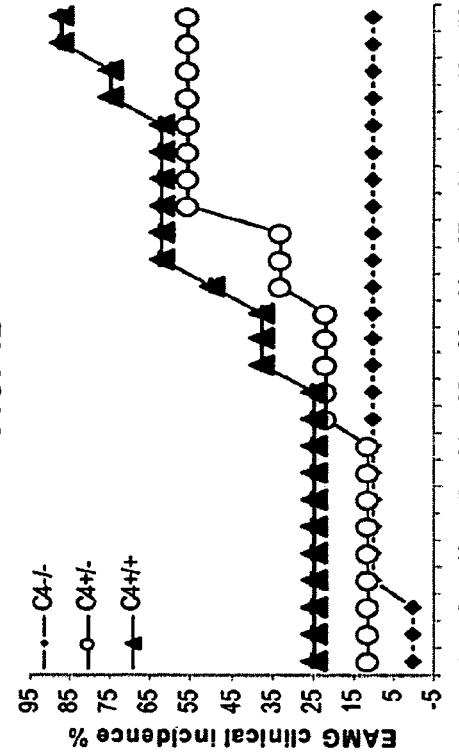
Figure 4C:
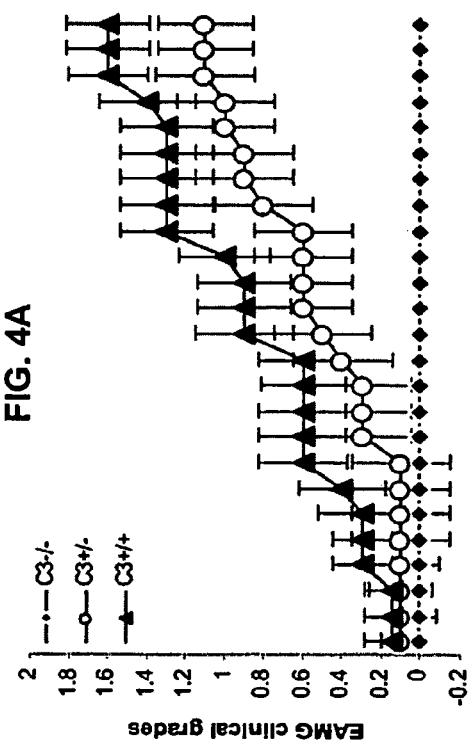
FIGS. 4C and 4D are graphs showing the effect of C4 gene deletion on clinical EAMG development in terms of EAMG severity (FIG. 4C) and EAMG incidence (FIG. 4D).
Figure 4D:
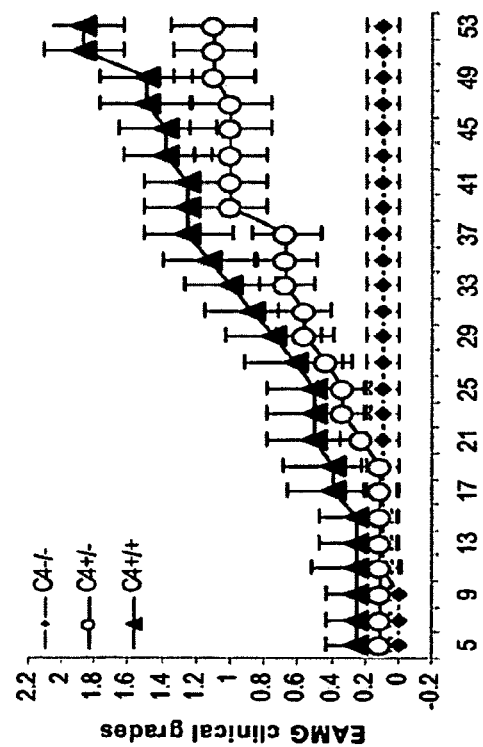

These findings suggest increased CD4+ T cells as the pivotal factor for increased EAMG incidence. These cells showed their effects possibly by increasing anti-AChR IgG levels and thus inducing a more severe form of EAMG. C3 and C1q-CIC are known to boost the production and proliferation of B and T cells, respectively. Altogether, C3, T cells, and antigen-specific IgG appear to enhance each other's production, creating a vicious circle and thus augmenting clinical disease. Such a hypothetical scenario of EAMG immunopathogenesis is depicted in FIG. 3. Building on this scenario, it was further hypothesized that one way of breaking this circle would be to decrease C3 levels by blocking the classical pathway.

EXAMPLE 3

Role of the Classical Complement Pathway in EAMG

To delineate the role of classical complement pathway in EAMG, C4 gene KO mice were immunized with AChR in CFA. C3 gene KO mice were used as positive control since C3 is a central complement factor and the initiator of the lytic pathway and C5 (another factor of the same pathway) deficient mice are highly resistant to EAMG (Christadoss, J. Immunol., 140(8):2589-2592 (1988), which is hereby incorporated by reference). To induce EAMG, $C3^{-/-}$, $C3^{+/-}$, $C3^{+/+}$, $C4^{-/-}$, $C4^{+/-}$, and $C4^{+/+}$ mice were immunized with AChR in CFA. $C3^{-/-}$ or $C4^{-/-}$ mice were highly resistant to EAMG (p values for clinical incidences, as compared to control littermates, were 0.0001 and 0.0005), whereas the disease incidences for $C3^{+/-}$, $C3^{+/+}$, $C4^{+/-}$, $C4^{+/+}$ mice were 63%, 86%, 56%, and 88%, respectively (FIGS. 4A-4D). These data provide the first direct genetic evidence for the involvement of C3, C4, and, thus, the classical complement pathway in the development of clinical EAMG following immunization with AChR.

Figure 5A:
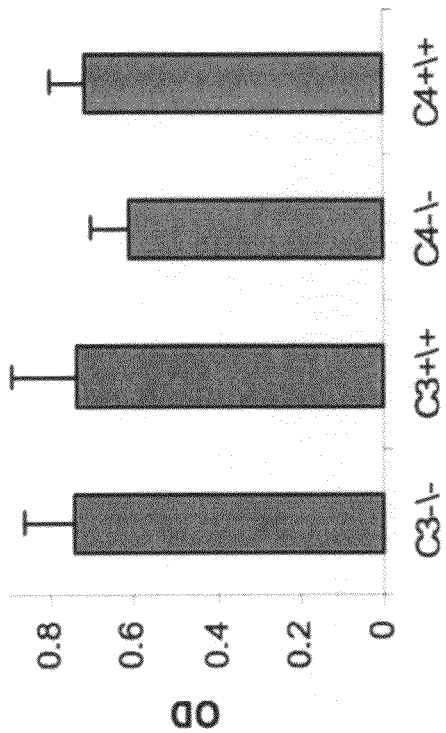
FIGS. 5A-5D are bar graphs showing serum anti-AChR levels in C3 and C4 knockout mice.
Figure 5B:
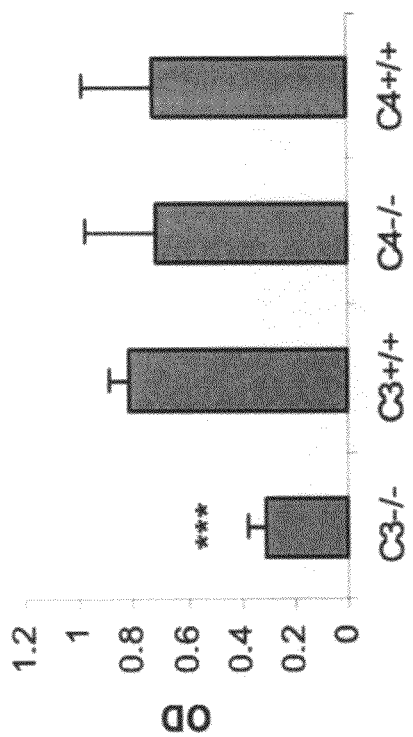
Figure 5C:
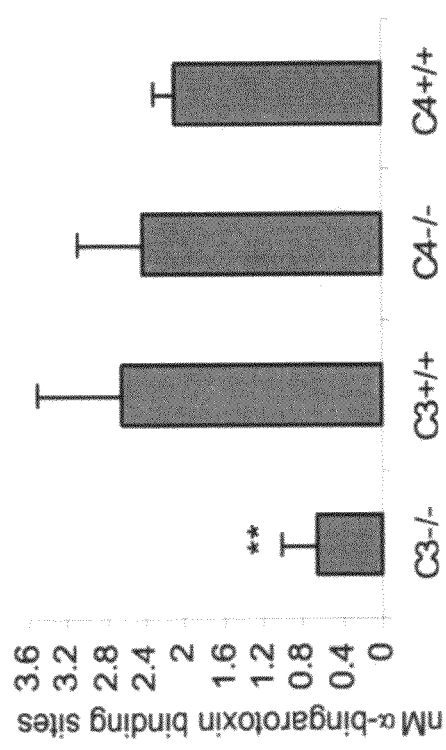
Figure 5D:
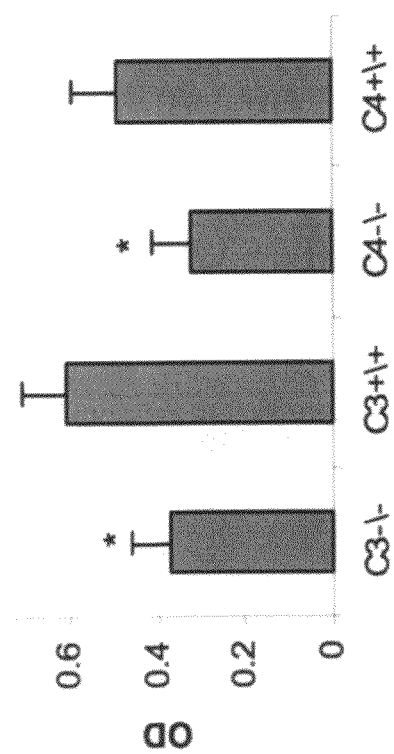

AChR-immunized $C4^{-/-}$ mice possessed similar amounts of total anti-AChR IgG levels in their serum samples as their control $C4^{+/+}$ littermates, whereas $C3^{-/-}$ mice displayed suppressed anti-AChR IgG production (p=0.0049) (FIG. 5A). On the other hand, IgG2b production against AChR was inhibited significantly in both $C3^{-/-}$ (p=0.047) and $C4^{-/-}$ mice (p=0.029) (FIG. 5C). These results reveal that, in $C4^{-/-}$ mice, EAMG resistance may also be related with diminished levels of complement-binding IgG2b antibodies. Total serum IgG and anti-AChR IgG1 levels were similar to those of control littermates in $C4^{-/-}$ mice (FIGS. 5B and 5D).

To further clarify the importance of C3 or C4 deficiency in EAMG resistance despite the presence of serum anti-AChR IgGs, we double-stained frozen muscle sections of all strains of mice with .alpha.-bungarotoxin (".alpha.-BTx") (which binds to NMJ) and antibodies directed against either IgG, C3, or MAC. All mice displayed IgG deposits on the NMJ and all $C3^{+/+}$ and $C4^{+/+}$ littermates had C3 and MAC deposits, whereas C3 and MAC deposits could not be detected on the NMJ of $C3^{-/-}$ and $C4^{-/-}$ mice (FIGS. 6A-6D). The absence of C3 and MAC deposits, despite the presence of IgG on the NMJ of $C3^{-/-}$ and $C4^{-/-}$ mice suggests that C3 and MAC are playing a critical role in NMJ destruction in EAMG. Additionally, IgG bound to the NMJ without complement is not sufficient to induce optimal AChR destruction and clinical EAMG. Thus, C4 gene deficiency prevented the induction of EAMG, without significantly affecting IgG production and with slight decreases in anti-AChR IgG2b levels.

EXAMPLE 4

The Hypothesis and In Vivo Testing Thereof

The experiments described in Example 3 suggest that classical complement pathway may be critical for the development of EAMG and, in mice with complement C4 gene deficiency, the disease incidence and severity can be extremely low. Based on these results, it was hypothesized that inhibition of the classical complement pathway would prevent and suppress established EAMG. To analyze the role of acquired classical complement deficiency, the hypothesis was tested that in vivo C1q depletion, achieved by administration of anti-C1q, would prevent induction of EAMG by AChR immunization in CFA and also suppress the established disease. The prevention experiments are set forth in Example 5, and the therapeutic treatment experiments are set forth in Example 6.

EXAMPLE 5

In Vivo Prevention Experiments Using Anti-C1q

Anti-C1q (mouse anti-human IgG) were obtained from hybridoma cell line 4A4B11 (ATCC Accession No. 1000617). The antibodies were acquired from the medium of the cultured cells, and they were purified by an affinity column procedure. Studies showed that administration of this antibody (0.2 mg/injection, twice weekly, starting 10 days before first immunization) caused a measurable decline in the clinical incidence and severity of EAMG. A non-specific mouse IgG antibody (Sigma) (applied in the same dosages as anti-C1q) was used as a negative control in all experiments.

Eight of each anti-C1q-treated and control-antibody-treated B6 mice (Jackson Laboratory) were immunized s.c. in foot pads and shoulders with 20 μg Torpedo AChR in CFA on day 0 and then were reimmunized s.c. in shoulders and thighs with the same amount of antigen on day 30. Anti-C1q or control antibody treatment (i.p.) was started 10 days before the first immunization with AChR in CFA with an initial dose of 200 μg. Then, treatment was continued with 100 μg/injection, twice weekly. Mice were screened for the development of clinical EAMG and were bled for serum on days 0, 15, and 45.

Figure 7A:
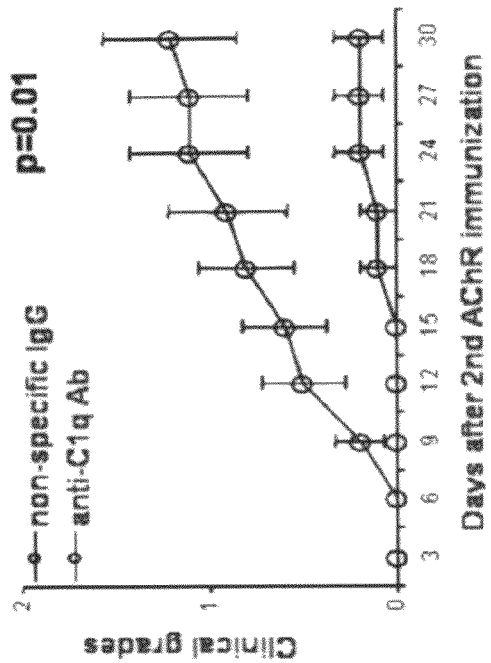
FIGS. 7A-7C are graphs showing that, relative to control IgG-treated mice, anti-C1q mice exhibit reduced incidence of EAMG induction (FIG. 7A), that anti-C1q-treated mice have less severe EAMG (FIG. 7B), and that anti-C1q-treated mice have significantly higher average grip strengths (FIG. 7C).
Figure 7B:
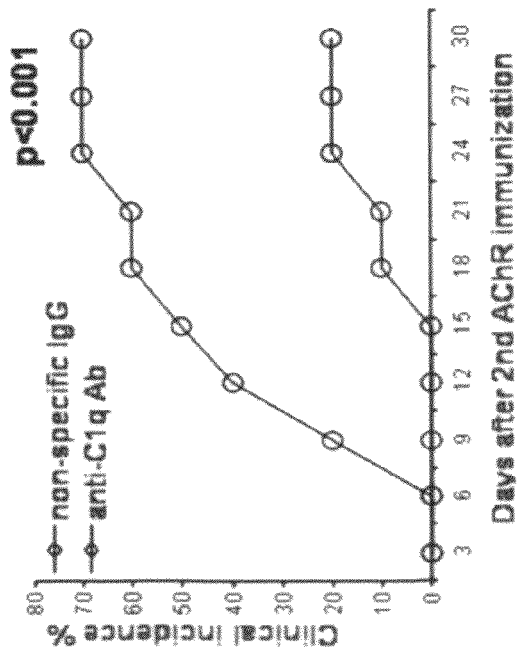
Figure 7C:
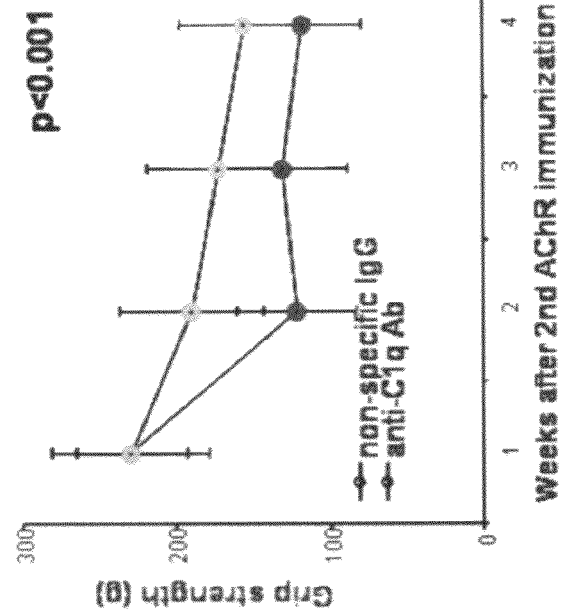
Figure 8A:
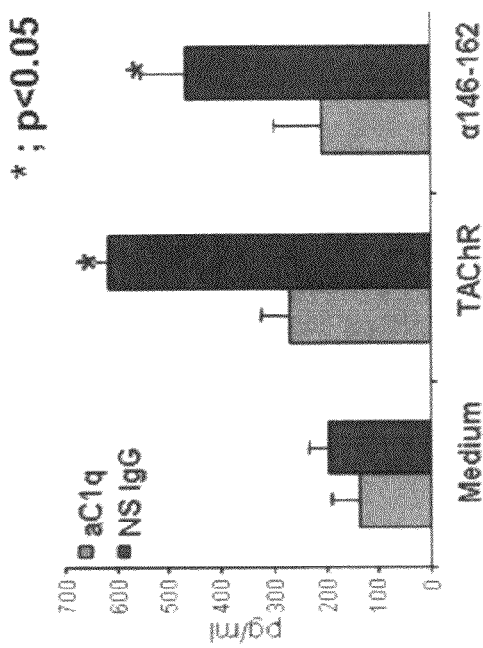
FIG. 8A-8D are bar graphs showing cytokine production profiles (IL-2 (FIG. 8A); IL-6 (FIG. 8B); IL-10 (FIG. 8C); and IFN-.gamma.
Figure 8B:
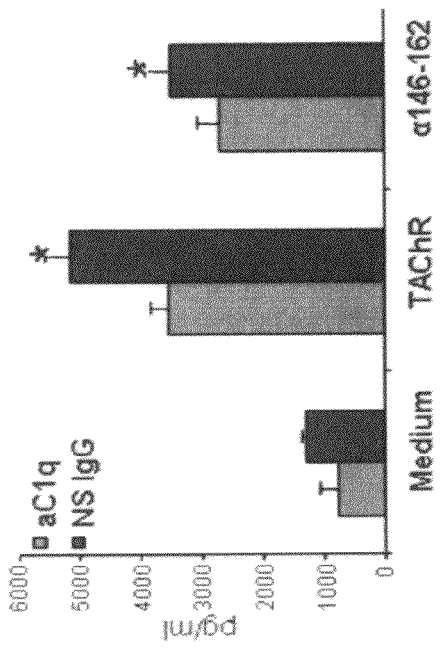
Figure 8C:
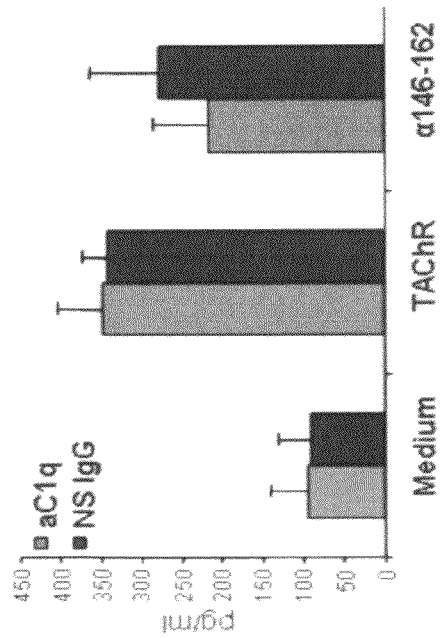
Figure 8D:
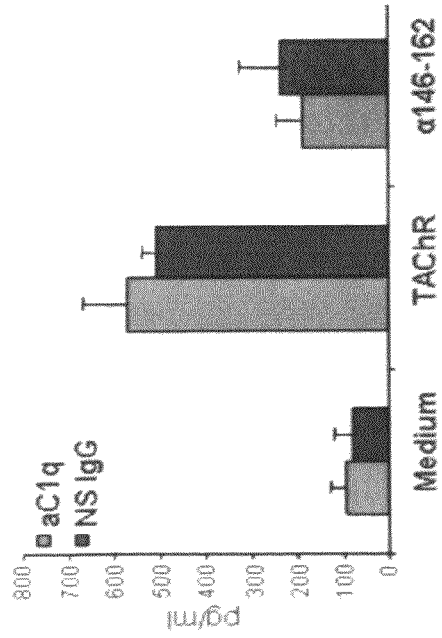

Anti-C1q treatment protected mice against EAMG induction, as shown in FIG. 7A. Briefly, EAMG incidence was 20% in anti-C1q-treated mice vs. 70% in control IgG-treated mice ($p<0.0001$). Also, as shown in FIG. 7B, anti-C1q-treated mice had less severe EAMG (i.e., significantly lower average clinical grades, $p=0.01$), compared to their control IgG-treated mice counterparts. Moreover, the average grip strength (an objective measure of muscle strength measured in a grip strength meter) of anti-C1q-treated mice remained significantly higher than that of control IgG-treated mice ($p<0.001$) (FIG. 7C). However, anti-C1q-treated mice still had lower average grip strength as compared to before-treatment values, suggesting, perhaps, that anti-C1q-treatment is considerably preventing EAMG induction, but, at the same time, the clinical worsening and possibly the NMJ AChR loss is going on, probably at a slower pace, as compared to control mice.

Figure 9:
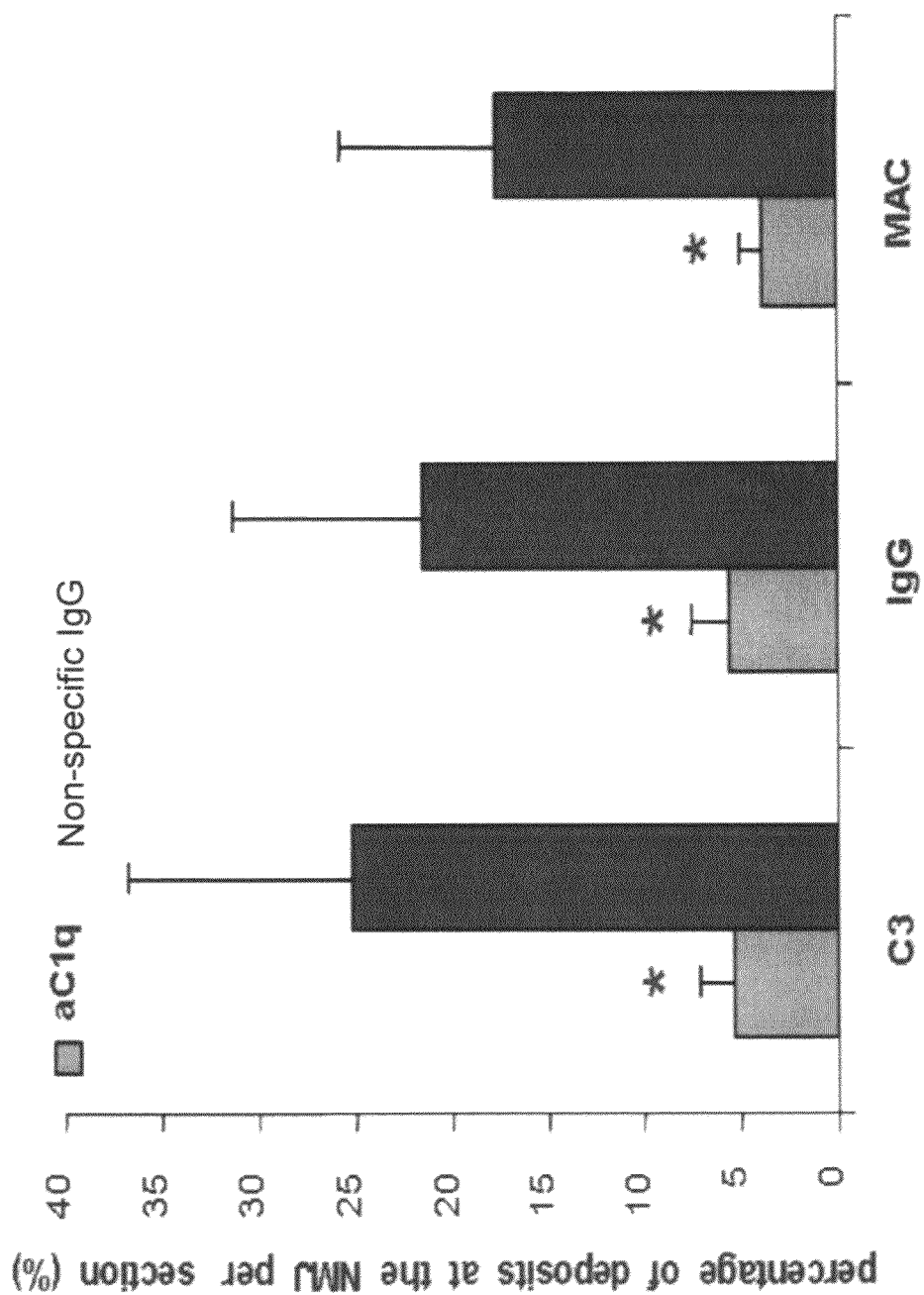
FIG. 9 is a bar graph showing the effect of anti-C1q treatment on NMJ complement and IgG deposition.

FIGS. 8A-8D show cytokine production profiles of anti-C1q-treated mice and control IgG-treated-mice. Suppression of EAMG in anti-C1q-treated mice was associated with lower IL-6 and IFN-gamma production by AChR- and/or immunodominant peptide .alpha.146-162-stimulated cultured lymph node cells ($p<0.05$, FIGS. 8B and 8D). Interestingly, AChR-immunized C3 KO mice also had lower IL-6 and IFN-.gamma. levels in their cultured lymph node cell supernatants. This is a notable finding, since IL-6 and IFN-.gamma. are important factors in EAMG pathogenesis (Karachunski et al., J. Immunol., 164(10):5236-5244 (2000); and Deng et al., J. Immunol., 169(2):1077-1083 (2002), which are hereby incorporated by reference). Additionally, anti-C1q-treated mice had lower C3, IgG, and MAC deposits at their NMJs (FIG. 9).

Flow cytometry analysis of the lymph node cells and immunohistochemistry performed on paraffin-embedded spleen sections revealed normal T cell and elevated B cell counts in lymph node cells (FIG. 10A) and normal PNA+ germinal center follicles in spleen sections of anti-C1q-treated mice (FIGS. 10B and 10C).

Figure 11:
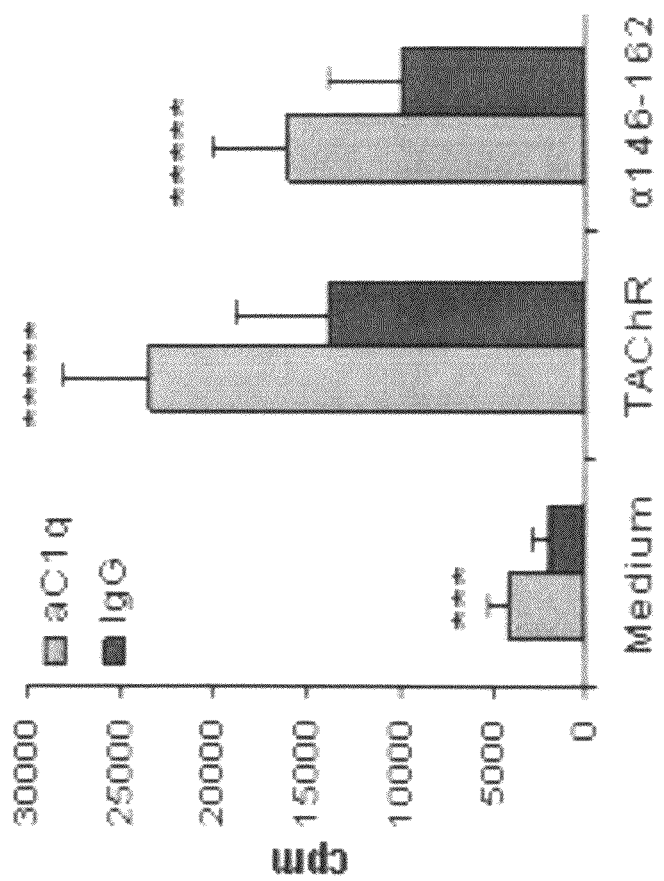
FIG. 11 is a bar graph showing lymph node cell proliferation in anti-C1q-treated mice and control IgG-treated mice.
Figure 13A:
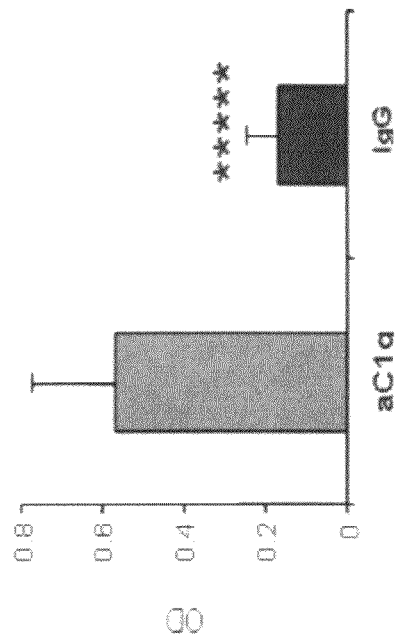
FIGS. 13A-13D are bar graphs showing serum C1q-CIC levels (FIG. 13A), serum C1q levels (FIG. 13B), serum C3 levels (FIG. 13C), and serum C3-CIC levels (FIG. 13B) in anti-C1q-treated mice and control IgG-treated mice.
Figure 13B:
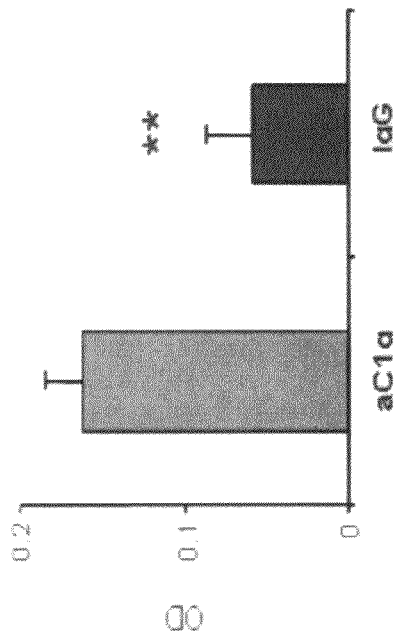
Figure 13C:
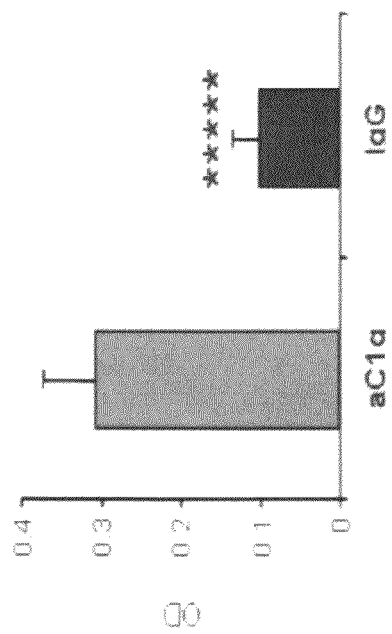
Figure 13D:
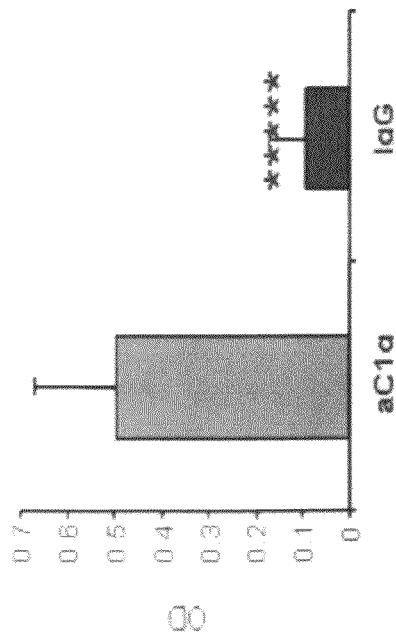

AChR-stimulated lymphocyte proliferation was not affected by anti-C1q-treatment (FIG. 11), suggesting that T and B cell functions were preserved. Interestingly, both PNA+ spleen germinal center follicles and proliferation capacity of lymph node cells were increased in anti-C1q-treated cells, which might be a reflection of stimulatory effects of increased levels of immune complexes on T and B cell proliferation.

On the other hand, anti-C1q-treated mice had an overall enhancement in the humoral response characterized by increased serum anti-AChR antibody levels (IgM, IgG, IgG1 isotypes) (FIGS. 12A-12F) and increased serum C1q, C3, and C3-conjugated immune complex levels (FIGS. 13A-13D). All experiments were repeated at least twice to ensure reproducibility of the data.

Despite elevated antibody and complement response, anti-C1q treatment ameliorated EAMG. This suggests that anti-C1q treatment might not be preventing EAMG by classical complement pathway blockade. Anti-C1q might be increasing the half-lives of C1q molecules or triggering a compensatory increase in C1q production and thus increasing classical pathway activation and consequent C3 production. Increased C3 and immune complex levels might be enhancing B cell antibody production. anti-C1q might rather be preventing EAMG induction by competing with immune complexes in the circulation and partially reducing lymph node cell IL-6 and IFN-gamma production. With a similar mechanism, anti-C1q might be preventing immune complex deposition and complement activation, which would eventually cause NMJ destruction (a hallmark of MG pathology). Then again, it is noteworthy that anti-C1q treatment does not cause a reduction in lymph node B and T cell counts, in sharp contrast with the currently available immunosuppressive drugs (e.g. steroids, azathioprine), which decrease T and B cell counts significantly.

EXAMPLE 6

In Vivo Treatment Experiments on Ongoing Clinical EAMG Using Anti-C1q

A preliminary treatment experiment was carried out by administering anti-C1q after two immunizations to test whether C1q inhibition is capable of treating EAMG after generation of autoimmune response to AChR, simulating MG patients after diagnosis. For this purpose, a group of B6 mice were immunized with 20 .mu.g AChR in CFA on days 0 and 30. Five of these mice with lowest grip strength and/or Grade 2 or 3 disease were selected for treatment experiments. One group ($n=3$) of mice with Grade 2 or 3 disease was treated i.p. with anti-C1q and a second group ($n=2$) was treated with the control antibody (non-specific mouse IgG). The treatment schedule was same as that performed in prevention studies (initial dose of 200 .mu.g, then, 100 .mu.g/injection, twice weekly). Before anti-C1q treatment and on days 15 and 45 after anti-C1q treatment, mice were bled via tail vein. Mice were regularly screened for clinical scores, and, 35 days after the initiation of anti-C1q treatment, they were terminated and immunopathological examinations were performed.

Although this is an experiment conducted with small numbers of mice for both groups, some of the preliminary results were noteworthy. The anti-C1q-treatment decreased the severity of EAMG in one out of three mice from Grade 2 to Grade 1, whereas the clinical condition of one mouse remained stable and 1 mouse continued to clinically deteriorate. Both mice in the control group went on developing more severe disease (one mouse developed Grade 2 disease and the other Grade 3). However, the average of the grip strengths in anti-C1q-treated mice was significantly higher than the control mice (FIG. 14).

Figure 15:
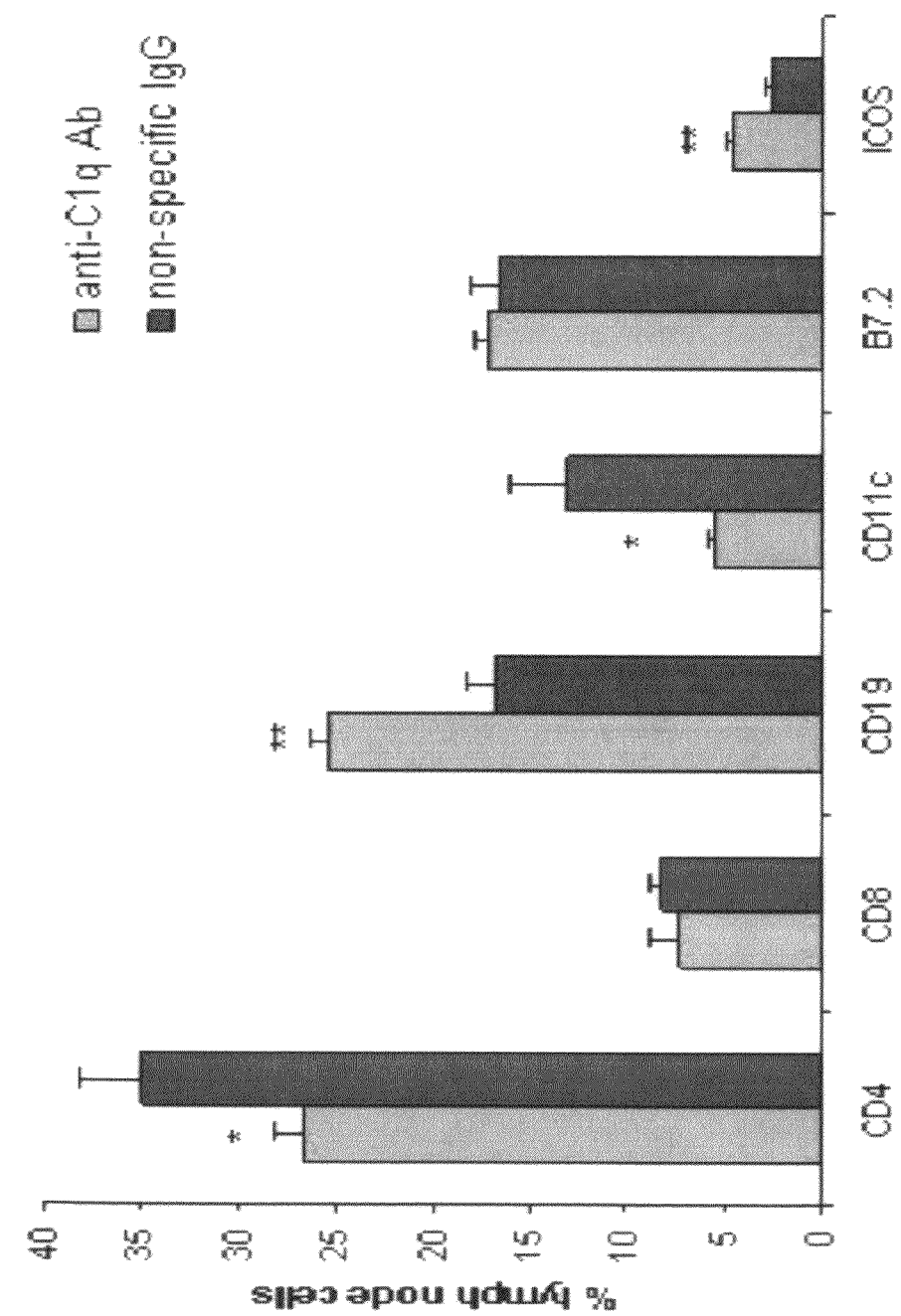
FIG. 15 is a bar graph showing lymph node cell profiles of mice afflicted with ongoing EAMG after treatment with anti-C1q or control IgG.
Figure 16:
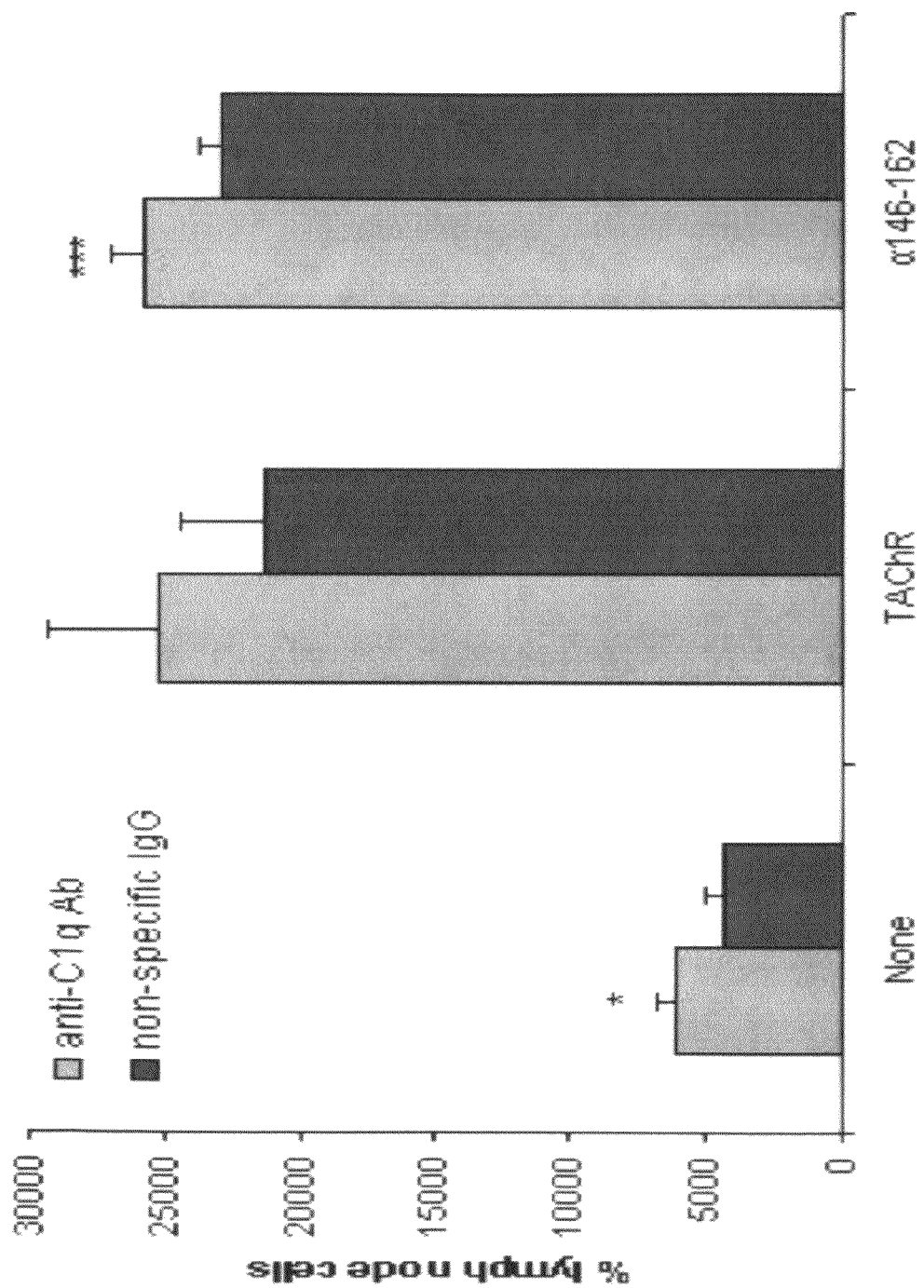
FIG. 16 is a bar graph showing lymph node cell proliferation in mice afflicted with ongoing EAMG after treatment with anti-C1q or control IgG.

A lymph node cell profile of the anti-C1q-treated ($n=3$) and control antibody-treated ($n=2$) mice is presented in FIG. 15. As FIG. 15 shows, anti-C1q-treatment was associated with the suppression of CD11c+ lymph node dendritic cells and an increase in CD19+ and ICOS+ cells in the lymph node. Dendritic cell suppression was particularly noteworthy since C1q is known to have inhibitory effects on dendritic cell functions. This might be associated with increased serum C1q levels due to anti-C1q treatment. Increase in CD19+ cells was similar to the increase observed in the prevention studies, proving, once again, the B cell stimulating potential of anti-C1q. In line with this finding, and similar to prevention studies, lymphocyte proliferation was significantly more pronounced in anti-C1q treated mice as compared to control mice (FIG. 16).

EXAMPLE 7

In Vivo Treatment Experiments on Ongoing Clinical EAMG Using C2 siRNAs

RT-PCR was used to confirm the suppression of C2 mRNA expression in EAMG mice following treatment with C2 siRNA. Mouse C2 siRNA (ON-TARGET plus SMART pool) was purchased from Dharmacon, Inc. Cat #L-048329-01. TransIT in vivo polymer solution, Cat #MIR 5100 was purchased from Mirus Biocorp. C2siRNA-polymer complex was prepared as per manufacturer's protocol.

Figure 17:
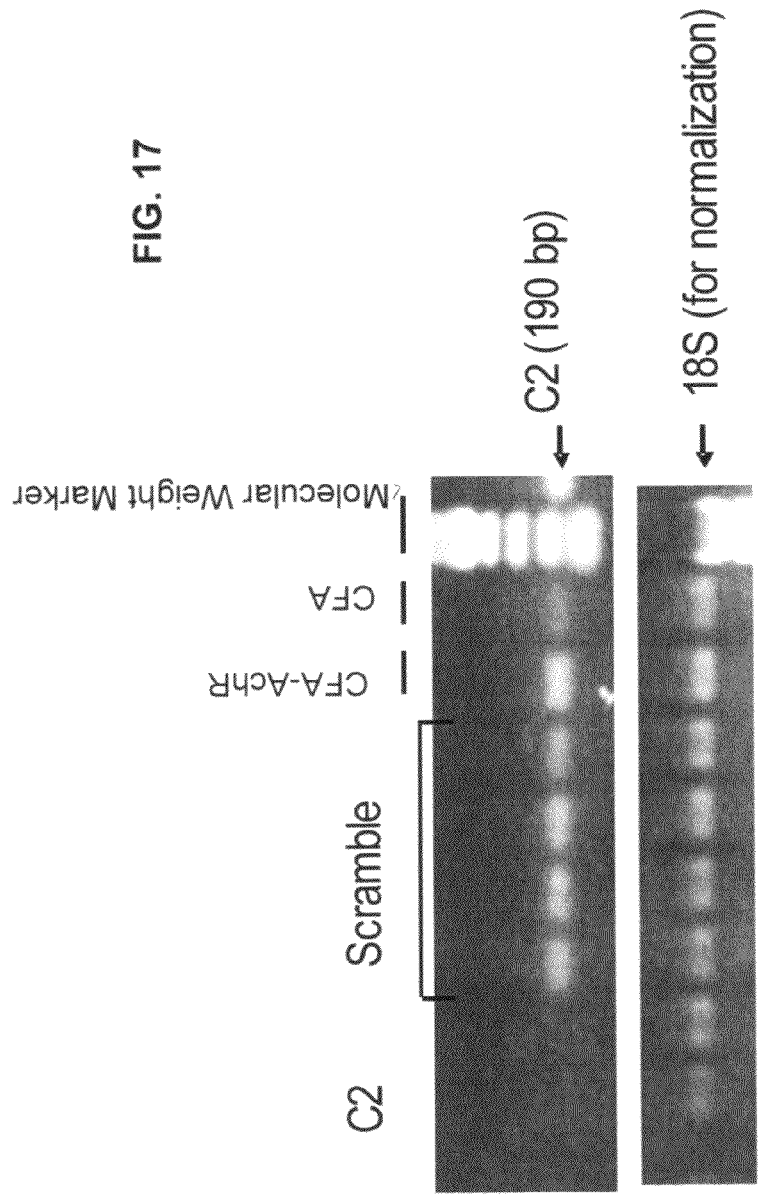
FIG. 17 is an image showing RT PCR detection of C2mRNA level in blood cells of EAMG mice following treatment with C2 small interfering RNA (siRNA).

In the first in vivo experiment, total RNA was isolated from blood cells from C57BL6 mice immunized and boosted with either CFA alone, or acetylcholine receptor (AChR) in CFA or AChR in CFA-immunized mice treated (i.p) either with C2 siRNA (20 μg) (2 mice) or scrambled siRNA (20 μg) (4 mice) conjugated to polymer. RT-PCR analysis (PCR product resolved in 1% agarose plus ethydium bromide) of cDNA revealed that C2 expression in two EAMG mice blood cells is completely inhibited by C2 siRNA at 72 h post-treatment (FIG. 17, lane 1 and 2).

Four days after the boost with AChR in CFA, EAMG C57BL6 mice were treated once either with C2 siRNA (10-20 μg) or scrambled siRNA (10-20 μg) in polymer. Limb muscle strength analysis with a digital grip meter showed a significant ($p=0.03$) improvement in grip strength of C2 siRNA-treated mice on day 16 post-siRNA treatment, compared to the scrambled siRNA-treated group (FIG. 18). C2 gene knockdown in blood cells is sufficient to treat clinical EAMG. A single injection of 10-20 μg C2 siRNA in polymer takes 16 days to produce a significant clinical improvement in muscle strength in mice with MG.

Figure 19C:
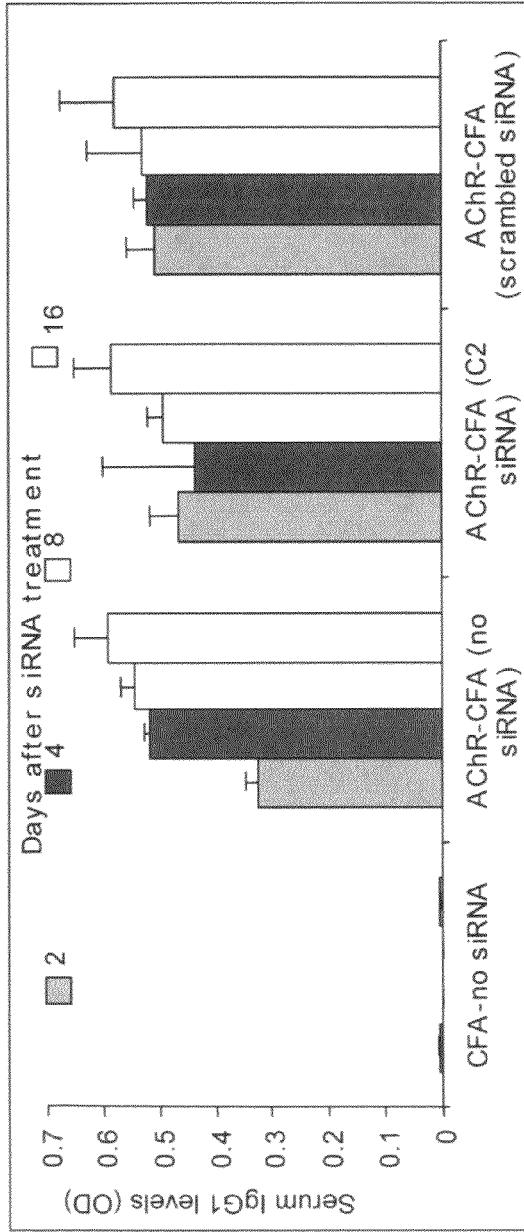
Figure 19D:
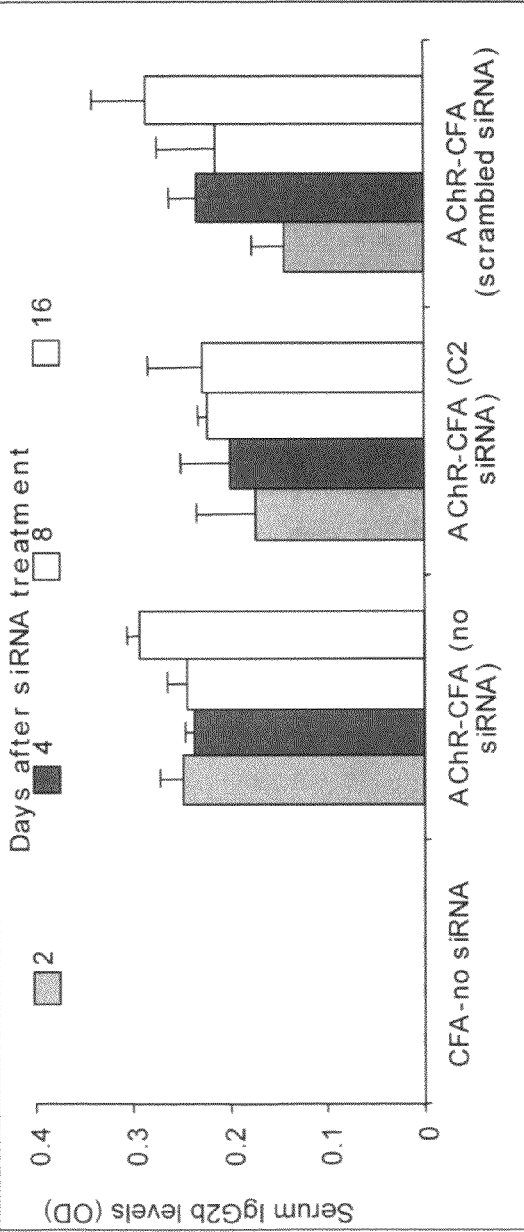

C2 siRNA treatment was shown to not influence production of anti-AChR antibody of IgG isotypes. Mice were bled on day 2, 4, 8 and 16 post C2- or scrambled siRNA-treatment from the tail vein, and serum was isolated and used in ELISA analysis with mouse AChR as coating antigen, HRPO-conjugated goat anti-mouse IgM or IgG isotypes as secondary antibodies and ABTS as substrate. There was no significant difference in anti-AChR IgG isotypes or IgM (OD) between C2 or scrambled siRNA-treated mice (FIG. 19 A-D). Therefore, C2 gene knockdown in blood cells is sufficient to treat clinical EAMG without suppressing anti-AChR antibody production.

Figure 20:
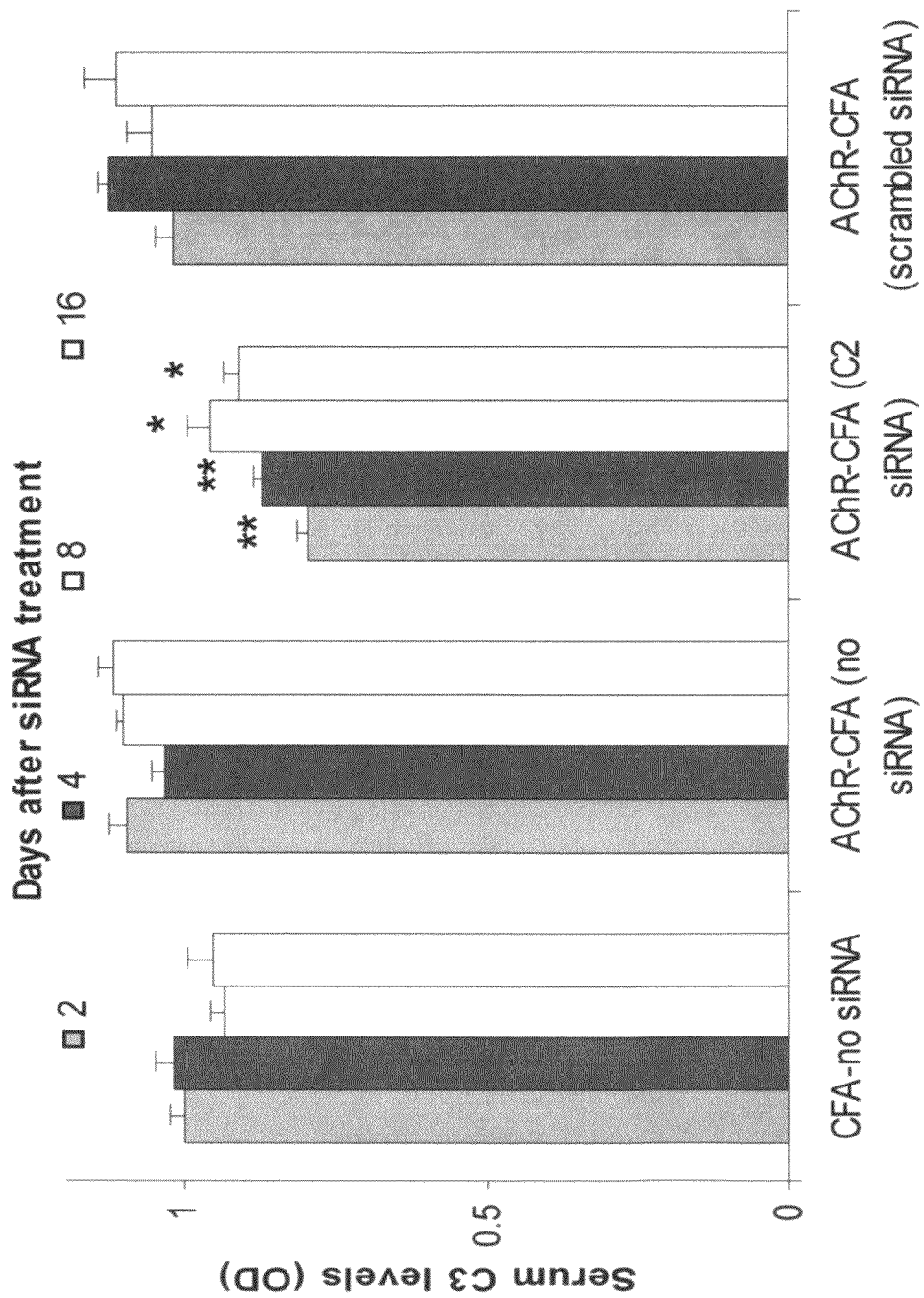
FIG. 20 is a bar graph showing reduced serum C3 level in C2 siRNA treated mice.

C2 siRNA treatment was shown to reduce serum C3 level. Following a single i.p. injection, C2 siRNA treated mice exhibited significantly reduced serum C3 levels as compared to scrambled siRNA treated or AChR immunized mice without siRNA treatment (FIG. 20; *, $p<0.05$; **, $p<0.01$)). The reduction in serum C3 levels might be due to siRNA mediated silencing of C2 production. Following AChR immunization, AChR antibodies are expected to activate the classical pathway and enhance serum C3 levels. Since the classical pathway of C2 inhibited mice can not be effectively activated with circulating antibodies, they tend to display reduced C3 levels.

C2 siRNA treatment was shown to not induce weight loss in mice. To observe any obvious side effects due to C2siRNA in polymer injection on body weight, mice treated with C2 siRNA were weighed. Four days after 1st boost with CFA or CFA-AChR, C57BL6 mice were treated once either with C2 siRNA or scrambled siRNA (10-20 μg). The difference in body weight (in gm) of C2 siRNA treated mice was not statistically significant on any of post-treatment days, compared to scrambled siRNA treated or CFA or CFA-AChR group (FIG. 21). Therefore, C2 siRNA-polymer injection did not produce any weight loss in mice.

Figure 22:
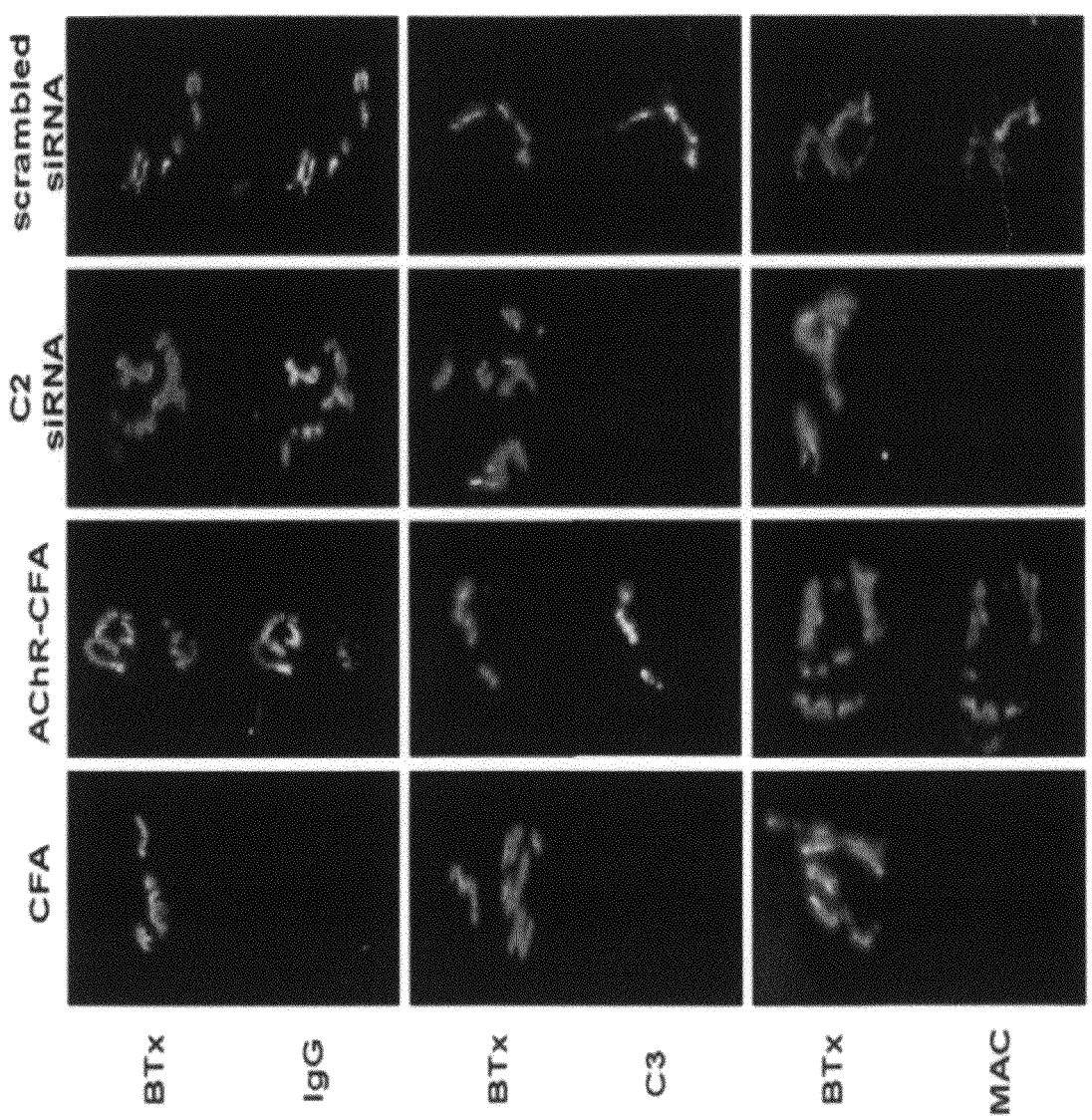
FIG. 22 depicts images showing resistance to EAMG in C2 siRNA treated mice is associated with the absence of C3 and MAC at their NMJs.
Figure 23:
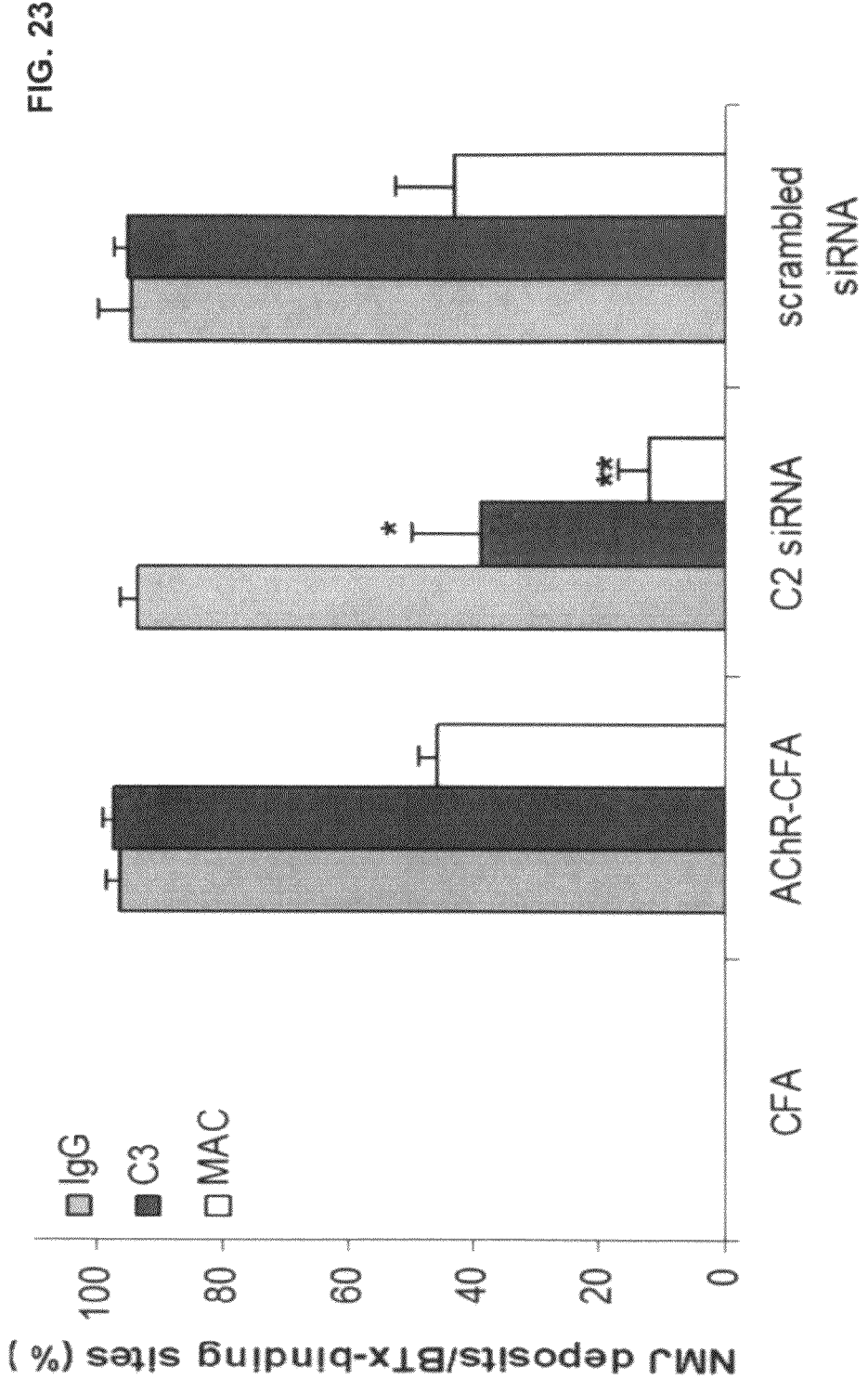
FIG. 23 is a bar graph showing AChR-CFA immunized mice treated with C2-siRNA show reduced NMJ C3 and MAC deposits as compared to AChR-CFA immunized mice treated with scrambled-siRNA or no siRNA.

Resistance to EAMG in C2 siRNA treated mice is associated with the absence of C3 and MAC at their NMJs (FIGS. 22 and 23). Muscle sections obtained from immunized B6 mice with or without siRNA treatment are stained for mouse IgG, C3 and MAC (all green fluorescence). The NMJs are localized by α-BTx (red fluorescence) (magnification for all, ×100). Although both scrambled siRNA and C2-siRNA treated mice reveal IgG binding, muscle sections of C2-siRNA treated mice are lacking C3 and MAC, which are crucial for disease induction. Non-siRNA-treated CFA and AChR-CFA immunized mice (left 2 columns) were used as negative and positive controls for NMJ deposits, respectively.

Figure 24:
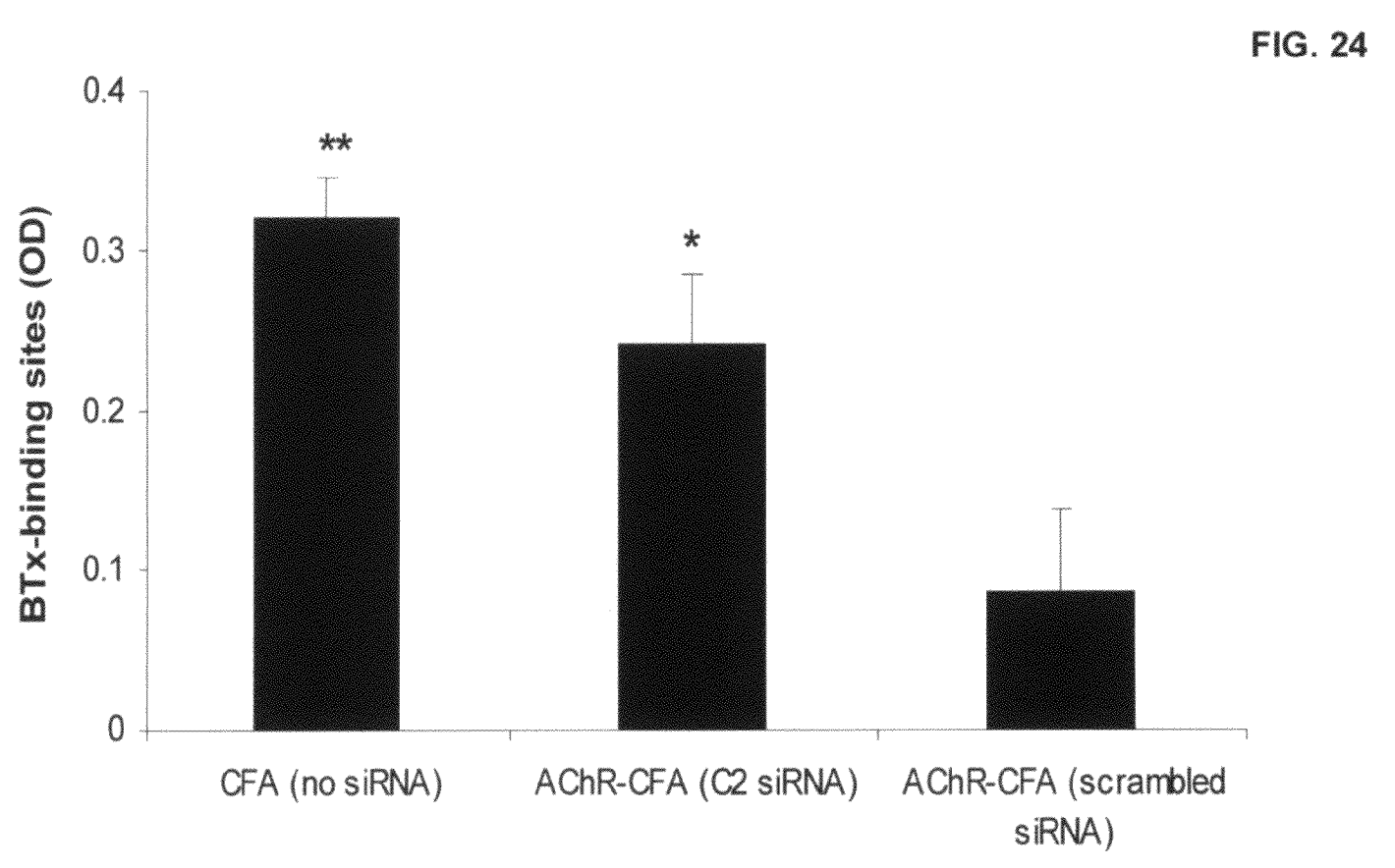

C2 siRNA treatment prevents AChR degradation in muscle following AChR immunization (FIG. 24). Mouse muscle extracts from individual mice were diluted 1/100 in carbonate/bicarbonate buffer, pH 9.6, and 100 μl were used to coat an ELISA plate overnight at 4° C. After washing, the BTx binding sites in the muscle extracts were detected by sequential addition of biotin-conjugated BTx (1:200, Molecular Probes) for 1 hour, avidin-peroxidase (1:400, Sigma-Aldrich) and ABTS solution (Roche) at room temperature. Results were expressed as arbitrary OD units. Both CFA-immunized B6 mice with no siRNA treatment and AChR-CFA immunized mice with C2 siRNA treatment showed preserved BTx-binding sites as compared to AChR-CFA immunized mice treated with scrambled siRNA. These results suggest that C2 siRNA treatment prevents AChR degradation following AChR immunization and treats myasthenia gravis in mice.

EXAMPLE 8

Discussion of the In Vivo Results

As observed from the in vivo prevention and treatment experiments described in Examples 5 and 6, anti-C1q appears to constitute a useful method to decrease the severity and incidence of EAMG without abolishing humoral immunity and antibody production and only partially blocking T cell cytokine production.

As noted above, anti-C1q treatment appears to increase serum C1q levels rather than decreasing them. Since C1q plays important roles in self-tolerance, clearance of immune complexes and apoptotic cells, and defense against infections, having increased serum C1q and C3 levels might be beneficial for the MG patients.

EAMG preventing efficiency obtained in the first two experiments proved to be more prominent, and anti-C1q-treated mice had much less severe EAMG. Therefore, anti-C1q therapy may find particular utility during MG remissions to prevent the exacerbation of disease. Currently, in general practice, MG patients who have undergone remission are still treated with very low doses of steroids for the fear of an imminent exacerbation. Anti-C1q may replace this treatment. It can also be used as an adjunct immunotherapy method for MG with acute and/or severe muscle weakness, for example, in addition to steroids and azathioprine. Additionally, increased immune complex levels observed in anti-C1q-treated mice are perturbing and might cause SLE-like immune complex diseases in the long run. In view of this, it may not be wise to attempt anti-C1q treatment in patients with lupus.

Further, a novel and efficient method was developed to treat MG and other complement-mediated diseases by using siRNA targeting the C2 gene involved in CP, thus preserving the alternative complement pathway to protect against microbial infection. This technology will have a major impact in treating complement-mediated autoimmune and inflammatory diseases and conditions in a specific manner with C2 siRNA with limited side effects.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for treating myasthenia gravis in a subject comprising the step of: administering to the subject a C2 small interfering RNA (siRNA) that inhibits the classical complement pathway.

2. The method of claim 1, wherein the sequence of the C2 small interfering RNA is a sequence having a sequence selected from the group consisting of SEQ ID NOs: 24-25, SEQ ID NOs: 27-28, SEQ ID NOs: 30-31 and SEQ ID NOs: 33-34.

3. The method of claim 1, wherein the C2 siRNA has a sequence of SEQ ID NOs:30-31.

* * * * *